US012593195B2

(12) United States Patent
Hanson et al.

(10) Patent No.: US 12,593,195 B2
(45) Date of Patent: Mar. 31, 2026

(54) SYSTEMS AND METHODS FOR DETECTING ILLEGITIMATE LOCATION DATA FOR A MONITORED INDIVIDUAL

(71) Applicant: BI Incorporated, Boulder, CO (US)

(72) Inventors: Duke Hanson, Boulder, CO (US); Ric Miller, Boulder, CO (US); Todd Bischoff, Boulder, CO (US)

(73) Assignee: BI Incorporated, Boulder, CO (US)

( * ) Notice: Subject to any disclaimer, the term of this patent is extended or adjusted under 35 U.S.C. 154(b) by 82 days.

(21) Appl. No.: 18/412,951

(22) Filed: Jan. 15, 2024

(65) Prior Publication Data

US 2024/0298144 A1     Sep. 5, 2024

Related U.S. Application Data

(60) Provisional application No. 63/449,919, filed on Mar. 3, 2023.

(51) Int. Cl.
| | |
|---|---|
| *G08B 1/08* | (2006.01) |
| *A61B 5/00* | (2006.01) |
| *A61B 5/11* | (2006.01) |
| *H04W 4/029* | (2018.01) |

(52) U.S. Cl.
CPC ........... *H04W 4/029* (2018.02); *A61B 5/1112* (2013.01); *A61B 5/681* (2013.01); *A61B 5/6898* (2013.01)

(58) Field of Classification Search
CPC ...... H04W 4/029; A61B 5/1112; A61B 5/681; A61B 5/6898
USPC ...................................... 340/539.13
See application file for complete search history.

(56) References Cited

U.S. PATENT DOCUMENTS

| | | | | |
|---|---|---|---|---|
| 11,410,529 | B2 * | 8/2022 | Barovič | ................ G08B 25/08 |
| 11,507,909 | B2 * | 11/2022 | Jones | ................... H04W 4/029 |
| 2005/0068169 | A1 * | 3/2005 | Copley | ............... G08B 29/046 |
| | | | | 340/568.1 |
| 2007/0229350 | A1 * | 10/2007 | Scalisi | ............... G08B 21/0272 |
| | | | | 342/350 |
| 2014/0320648 | A1 * | 10/2014 | Sager | ................... G08B 23/00 |
| | | | | 340/870.01 |

* cited by examiner

*Primary Examiner* — Tai T Nguyen
(74) *Attorney, Agent, or Firm* — Osha Bergman Watanabe & Burton LLP

(57) ABSTRACT

Various embodiments provide systems and methods for determining the veracity of location data gathered about a monitored individual.

20 Claims, 16 Drawing Sheets

100

200

300

400

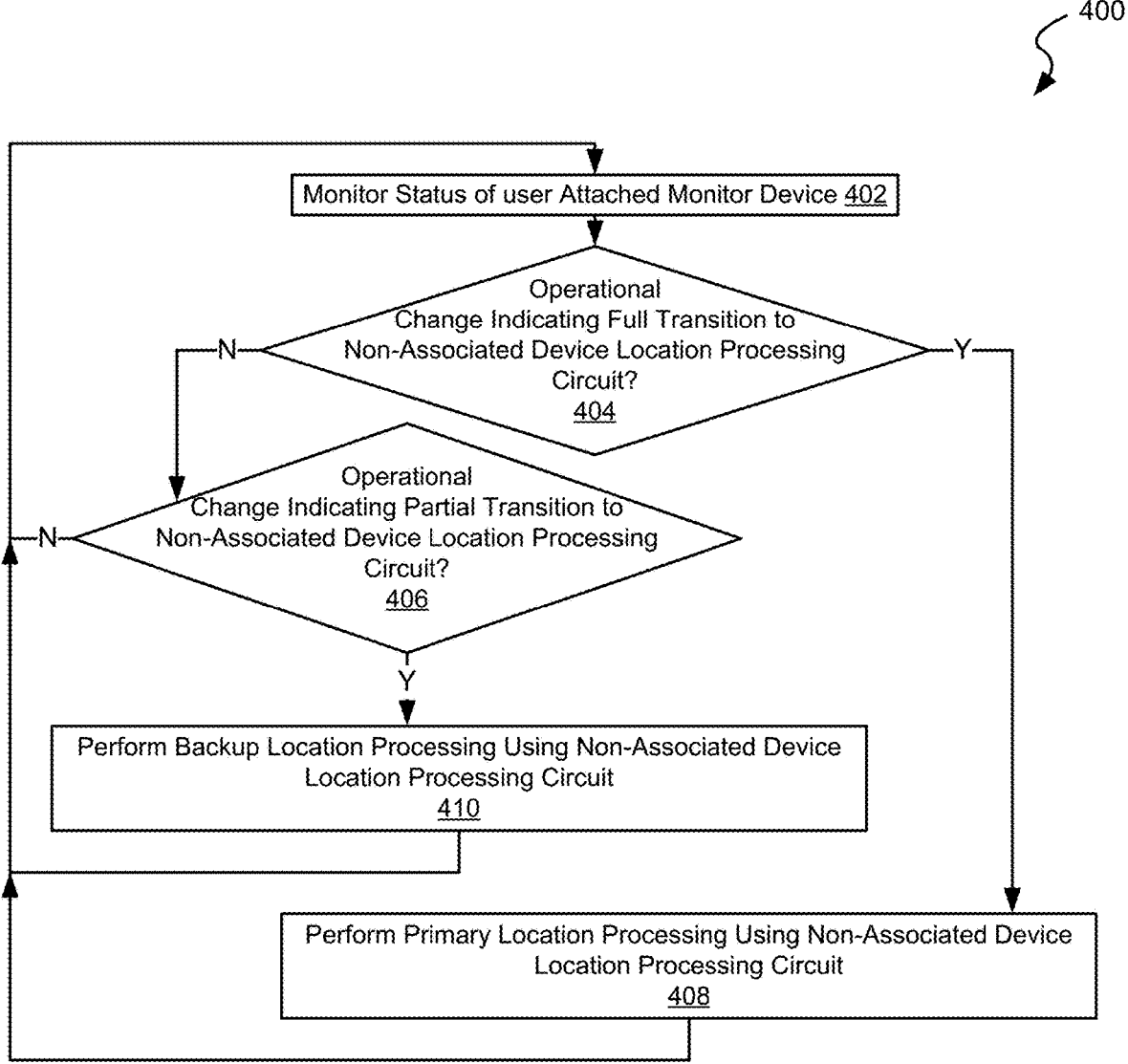

Monitor Status of user Attached Monitor Device 402

Operational
Change Indicating Full Transition to
Non-Associated Device Location Processing
Circuit?
404

Operational
Change Indicating Partial Transition to
Non-Associated Device Location Processing
Circuit?
406

Perform Backup Location Processing Using Non-Associated Device
Location Processing Circuit
410

Perform Primary Location Processing Using Non-Associated Device
Location Processing Circuit
408

Fig. 4

SYSTEMS AND METHODS FOR DETECTING ILLEGITIMATE LOCATION DATA FOR A MONITORED INDIVIDUAL

CROSS REFERENCE TO RELATED APPLICATIONS

The present application claims priority to (is a non-provisional application of) U.S. Pat. App. No. 63/449,919 entitled "Systems and Methods for Using Intermittent, Mobile Source Location Derived from Devices Not Associated with a Tracked Device and/or Tracked Individual to Define Location and Movement of the Tracked Individual", and filed Mar. 3, 2023 by Hanson et al. The entirety of the aforementioned reference is incorporated herein by reference for all purposes.

BACKGROUND OF THE INVENTION

Various embodiments provide systems and methods for utilizing third-party location information in relation to individual tracking.

Tracking devices have been attached to monitored individuals and provide an ability to automatically determine the location of the respective monitored individual. Such tracking devices can include, for example, location determination circuitry. Such location determination circuitry depends upon, for example, signal reception from location satellites, WiFi devices, and/or transmitting beacons. Each of these types of location services use differing levels of power to establish a location of a tracking device. Where power is depleted to a defined extent or the device is manipulated, such location determination circuitry can operate improperly causing a loss of location information from the tracking device.

Thus, for at least the aforementioned reasons, there exists a need in the art for more advanced approaches, devices and systems for detecting monitored individual location.

BRIEF SUMMARY OF THE INVENTION

Various embodiments provide systems and methods for utilizing third-party location information in relation to individual tracking.

This summary provides only a general outline of some embodiments. Many other objects, features, advantages and other embodiments will become more fully apparent from the following detailed description, the appended claims and the accompanying drawings and figures.

BRIEF DESCRIPTION OF THE DRAWINGS

A further understanding of the various embodiments may be realized by reference to the figures which are described in remaining portions of the specification. In the figures, similar reference numerals are used throughout several drawings to refer to similar components. In some instances, a sub-label consisting of a lower-case letter is associated with a reference numeral to denote one of multiple similar components. When reference is made to a reference numeral without specification to an existing sub-label, it is intended to refer to all such multiple similar components.

FIG. 4 is a flow diagram showing a method in accordance with some embodiments for utilizing non-associated device-based location in relation to other location methods;

DETAILED DESCRIPTION OF THE INVENTION

Figure 1A:
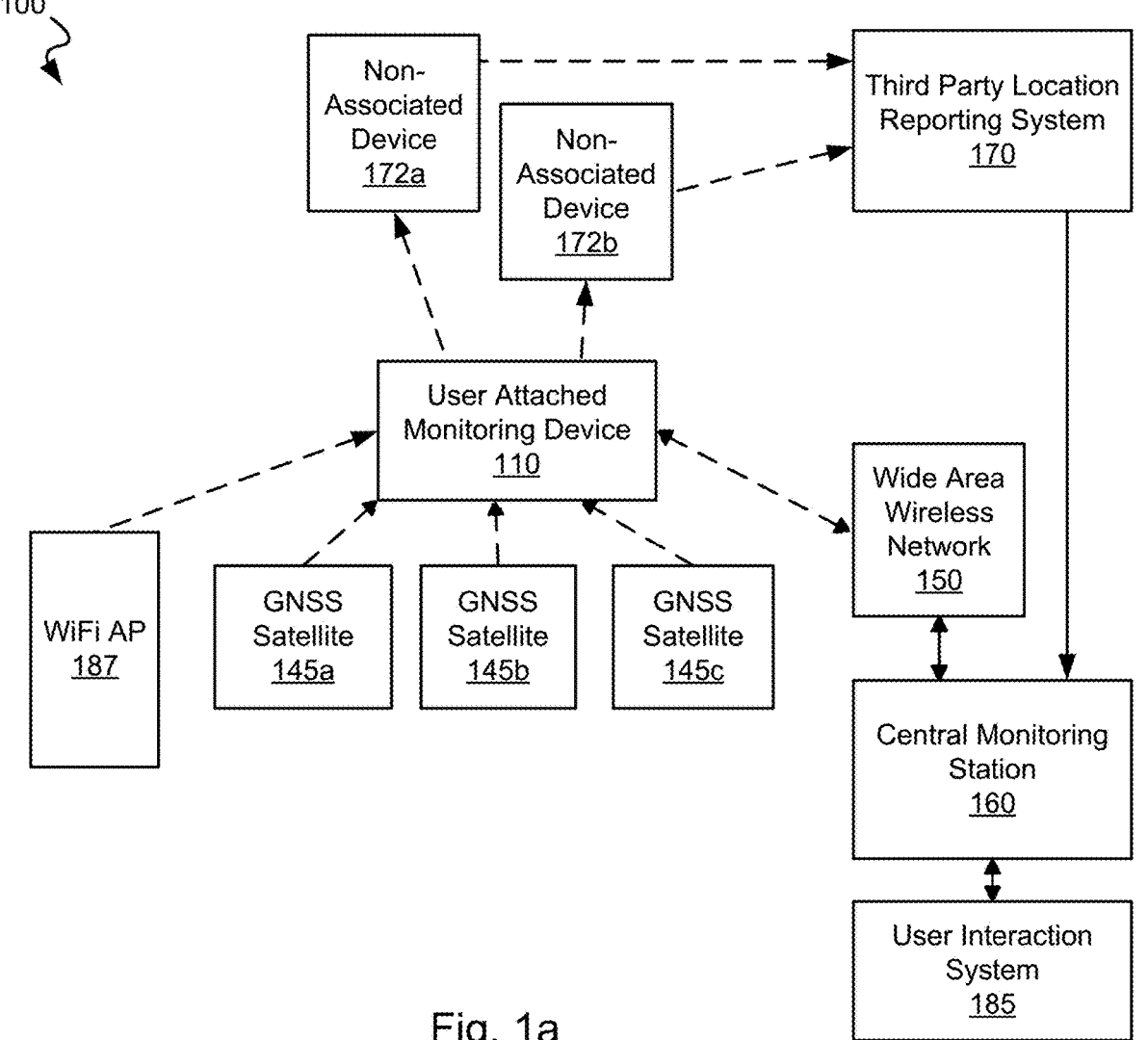
FIGS. 1a-1d are block diagrams illustrating a location monitoring system that includes a user attached monitoring device having WiFi access point-based location determination circuitry, satellite-based location determination circuitry, and non-associated device-based location determination circuitry in accordance with various embodiments.

Various embodiments provide systems and methods for utilizing third-party location information in relation to individual tracking.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

It is to be understood that the singular forms "a," "an," and "the" include plural referents unless the context clearly dictates otherwise. Thus, for example, reference to "cell" includes reference to one or more of such cells.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It is to be understood that one or more of the elements shown in the flowchart may be omitted, repeated, and/or performed in a different order than the order shown. Accordingly, the scope disclosed herein should not be considered limited to the specific arrangement of steps shown in the flowchart.

Although multiple dependent claims are not introduced, it would be apparent to one of ordinary skill that the subject matter of the dependent claims of one or more embodiments may be combined with other dependent claims.

In the following description of FIGS. 1-11, any component described with regard to a figure, in various embodiments disclosed herein, may be equivalent to one or more like-named components described with regard to any other figure. For brevity, descriptions of these components will not be repeated with regard to each figure. Thus, each and every embodiment of the components of each figure is incorporated by reference and assumed to be optionally present within every other figure having one or more like-named components. Additionally, in accordance with various embodiments disclosed herein, any description of the components of a figure is to be interpreted as an optional embodiment which may be implemented in addition to, in conjunction with, or in place of the embodiments described with regard to a corresponding like-named component in any other figure.

As used herein, the term "non-associated device" means any device that is not controlled by a monitoring device or an individual associated with the monitoring device and capable of transmitting its location information to a third-party location reporting system. Such a third-party location reporting system may be a crowd sourced location system as are known in the art. As an example, a third-party location reporting system may be the crowd sourced location system provided by Apple™. Non-associated devices may be, but are not limited to, mobile telephones, smart watches, or the like that are registered to provide location information to a third-party location reporting system. Based upon the disclosure provided herein, one of ordinary skill in the art will recognize a variety of devices that may be used as non-associated devices, and a variety of systems that may include both non-associated devices and a third-party reporting system used for identifying the location of a monitoring device that has provided identifications to one or more non-associated devices.

Various embodiments provide a wrist-worn impairment detection monitor. In some cases, such a wrist-worn impairment detection monitor is capable of rendering a likelihood that a wearer of the wrist-worn impairment detection monitor is impaired. The wrist-worn impairment detection monitoring has a variety of input sensors that can be used in relation to impairment detection processing capabilities to determine an impairment status of an individual.

Various embodiments provide methods for tracking a monitoring device that include: monitoring an operational status of the monitoring device to yield at least a first operational status of the monitoring device; based at least in part on the first operational status of the monitoring device, enabling a non-associated device-based location processing in the monitoring device. The non-associated device-based location processing includes communicating a data set identifying the monitoring device to a non-associated device within communication range of the monitoring device. In such a case, the location of the non-associated device is used as a proxy for the location of the monitoring device. In some instances of the aforementioned embodiments, the non-associated device is a mobile phone associated with a third-party location service.

In various instances of the aforementioned embodiments, the monitoring device is a user attached monitoring device including a securing mechanism configured to secure the user attached monitoring device to a monitored individual. In some instances of the aforementioned embodiments, the monitoring device is a user attached monitoring device, and the user attached monitoring device is configured to perform direct location processing. Such direct location processing is selected from one or more of: satellite-based location processing, and WiFi based location processing. In some such instances, the methods further include: based at least in part on the first operational status of the monitoring device, disabling the direct location processing.

In some instances of the aforementioned embodiments, the first operational status of the monitoring device is one of: a power status of the monitoring device, or a tamper status of the monitoring device. In various instances of the aforementioned embodiments, the first operational status of the monitoring device is a power status of the monitoring device, and enabling the non-associated device-based location processing in the monitoring device is based upon a combination of the power status of the monitoring device and a likelihood that the monitoring device is within communication range of two or more non-associated devices. In some instances of the aforementioned, the first operational status of the monitoring device is a tamper status of the monitoring device, and enabling the non-associated device-based location processing in the monitoring device is based upon a combination of the tamper status of the monitoring device and at least one of: a motion status of the monitoring device, or a biometrics status of the monitoring device. In various instances of the aforementioned embodiments, the first operational status of the monitoring device is a tamper status of the monitoring device, wherein the monitoring device is a user attached monitoring device attached to a monitored individual, and enabling the non-associated device-based location processing in the monitoring device is based upon a combination of the tamper status of the monitoring device and a communication status with a user detached monitoring device associated with the monitored individual. In some such instances the user detached monitoring device is a mobile phone.

Other embodiments provide tracking systems that include: a monitoring device associated with a monitored individual, a processor, and a computer readable medium. The monitoring device includes: a non-associated device-based location processing circuit; and a direct location processing circuit. The direct location processing circuit is one of a satellite-based location processing circuit, and/or WiFi based location processing circuit. The computer readable medium has stored therein instructions which when executed by the processor cause the processor to: monitor an operational status of the monitoring device to yield at least a first operational status of the monitoring device; based at least in part on the first operational status of the monitoring device, enable the non-associated device-based location processing circuit in the monitoring device. The non-associated device-based location processing circuit is configured to: communicate a data set identifying the monitoring device to a non-associated device within communication range of the monitoring device, and rely upon the non-associated device to report a location of the non-associated device as a location of the monitoring device to a recipient device.

Some embodiments provide methods for identifying questionable tracking data. Such methods include: receiving a first location data from a user detached monitor device and receiving a second location data from a third-party location service. The first location data includes a first location of the user detached monitor device obtained at a first time, and the user detached monitor device is configured to connect to a user attached monitor device. The second location data includes a second location obtained at a second time of a non-associated device to which the user attached monitor device connected. The methods further include: determining, by a processing resource, that the first time is within a time range of the second time; determining, by the processing resource, that a distance between the first location and the second location is greater than an expected distance; and indicating, by the processing resource, a questionable location from the user detached monitor device based at least in part on the distance between the first location and the second location being greater than the expected distance. In various instances, the expected distance is user programmable and/or the time range is user programmable.

In some instances of the aforementioned embodiments, the user attached monitor device is configured to connect to the user detached monitor device within a first maximum distance, and the user attached monitor device is configured to connect to non-associated device within a second maximum distance. In some cases, the first maximum distance is the same as the second maximum distance. In other cases, the first maximum distance is different from the second maximum distance. In various cases, the first maximum distance is less than five meters and the second maximum distance is less than ten meters. In some cases, the expected distance is greater than or equal to a sum of the first maximum distance and the second maximum distance.

In various instances of the aforementioned embodiments, the first location data includes a time stamp indicating when the first location was obtained and a device identification of the user attached monitor device. In some instances of the aforementioned embodiments, the second location data includes a time stamp indicating when the second location was obtained and a device identification of the user attached monitor device. In various instances of the aforementioned embodiments, the processing resource is communicably coupled to a display, and indicating the questionable location from the user detached monitor device includes displaying a message indicating the questionable location on the display.

Other embodiments provide monitoring systems that include: a user attached monitor device, a first wireless device, and central monitoring station. The user attached monitor device includes: a strap configured for attachment to a monitored individual; a wireless transceiver configured to connect to a first wireless device within a first defined range and a second wireless device within a second defined range; and a status indicator configured to detect a status of the user attached monitor device. The first wireless device is assigned to the monitored individual and includes: a first location subsystem configured to obtain a first location of the first wireless device; and a clock configured to time stamp the first location with a first time corresponding to obtaining the first location. The central monitoring station configured to: receive the first time and the first location directly from the first wireless device; receive a second location of the second wireless device and a time stamp for the second location from a third party location service with which the second wireless device is associated; determine that the first time is within a time range of the second time; determine that a distance between the first location and the second location is greater than an expected distance; and indicate a questionable location from the user detached monitor device based at least in part on the distance between the first location and the second location being greater than the expected distance.

Yet other embodiments provide user attached monitor devices. Such devices include: a strap configured for attachment to a monitored individual; a wireless transceiver configured to connect to a first wireless device within a first defined range and a second wireless device within a second defined range, wherein the first defined range is less than the second defined range; and a status indicator configured to detect a status of the user attached monitor device. The status of the user attached monitor device includes one or more of: occurrence of a timeout condition; detection of tampering with the user attached monitor device, and/or a change in proximity between the user attached monitor device and the monitored individual. The power of the wireless transceiver is increased to connect out to the second defined range based at least in part on the status of the user attached monitor device.

Turning to FIG. 1a, a block diagram illustrates a monitoring system 100 including a user attached monitor device 110 and a central monitoring station 160. Central monitoring station 160 is wirelessly coupled to user attached monitor device 110 via one or more wide area wireless (e.g., cellular telephone network, Internet via a WiFi access point, or the like) communication networks 150.

Central monitoring station 160 may be any location, device or system where location data and/or other types of data are received, including by way of non-limiting example: a cellular/smart phone, an email account, a website, a network database, and a memory device. The location data and/or other types of data are stored by central monitoring station 160 and are retrievable by a monitoring individual, such as a parent, guardian, parole officer, court liaison, spouse, friend, or other authorized group or individual. In this manner, the monitoring individual is able to respond appropriately to detected activity of a monitored individual. In some cases, the monitoring individual is able to retrieve the location data and/or other data types via a user interaction system 185 which may be, but is not limited to, a network connected user interface device communicatively coupled via a network to central monitoring station 160 and/or directly to user attached monitor device 110 via wide area wireless network 150.

Central monitoring station 160 may include a server supported website, which may be supported by a server system comprising one or more physical servers, each having a processor, a memory, an operating system, input/output interfaces, and network interfaces, all known in the art, coupled to the network. The server supported website comprises one or more interactive web portals through which the monitor may monitor the location of the monitored individual in accordance with the described embodiments. In particular, the interactive web portals may enable the monitor to retrieve the location and user identification data of one or more monitored individuals, set or modify 'check-in' schedules, and/or set or modify preferences. The interactive web portals are accessible via a personal computing device, such as for example, a home computer, laptop, tablet, and/or smart phone.

In some embodiments, the server supported website comprises a mobile website or mobile application accessible via a software application on a mobile device (e.g. smart phone).

The mobile website may be a modified version of the server supported website with limited or additional capabilities suited for mobile location monitoring.

User attached monitor device 110 includes a location sensor that senses the location of user attached monitor device 110 and generates corresponding location data. For example, when user attached monitor device 110 is capable of receiving wireless global navigation satellite system (hereinafter "GNSS") location information 136, 138, 139 from a sufficient number of GPS or GNSS satellites 145 respectively, user attached monitor device 110 may use the received wireless GNSS location information to calculate or otherwise determine the location of a human subject to which user attached monitor device 110 is attached. Global positioning system (hereinafter "GPS) is one example of a GNSS location system. While GPS is used in the specific embodiments discussed herein, it is recognized that GPS may be replaced by any type of GNSS system. In some instances, this location includes latitude, longitude, and elevation. It should be noted that other types of earth-based triangulation may be used in accordance with different embodiments of the present invention. For example, other cell phone-based triangulation, UHF band triangulation such as, for example, long range (hereinafter "LoRa") triangulation signals. Based on the disclosure provided herein, one of ordinary skill in the art will recognize other types of earth-based triangulation that may be used. The location data may comprise one or more of, but is not limited to: global positioning system ("GPS") data, Assisted GPS ("A-GPS") data, Advanced Forward Link Trilateration ("AFLT") data, and/or cell tower triangulation data. Where GPS is used, user attached monitor device 110 receives location information from three or more GPS or GNSS satellites 145 via respective communication links 136, 138, 139. The location data and/or other data gathered by user attached monitor device 110 is wirelessly transmitted to central monitoring station 160 via wide area wireless network 150 accessed via a wireless link 135.

Further, user attached monitor device 110 includes WiFi based location determination circuitry that is configured to communicate with one or more WiFi access points 187, and based thereon to determine location of user attached monitor device 110.

Yet further, user attached monitor device 110 includes non-associated device-based location determination circuitry that is configured to sense that one or more non-associated devices 172 (e.g., a non-associated device 172a and/or a non-associated device 172b) is/are within range of user attached monitor device 110, and to communicate (i.e., transmit) an identification of user attached monitor device 110 to the identified non-associated device. In some embodiments, the aforementioned communications are performed via BlueTooth™ or another relatively short-range, low-power communication protocol. Based upon the disclosure provided herein, one of ordinary skill in the art will recognize a variety of protocols that may be used for communications between user attached monitor device 110 and a nearby non-associated device 172.

In turn, the non-associated device that received the identification information from user attached monitor device 110 reports the identification received from user attached monitor device 110 and the location of the non-associated device to a third-party location reporting system 170. Third-party location reporting system 170 in turn transfers the received identification and location information to a recipient registered with the received identification in third-party location reporting system 170. In this case, the recipient registered with the received identification in third-party location reporting system 170 is central monitoring station 160. In such a case, a location of the non-associated device that provided the identification of user attached monitor device 110 to third-party location reporting system 170 is established by central monitoring station 160 as the location of user attached monitor device 110. The power requirements of the user attached monitor device 110 for identifying the non-associated device and communicating the identification to the non-associated device are less than that required to determine location based either on WiFi access points 187 or GNSS satellites 145.

Figure 1B:
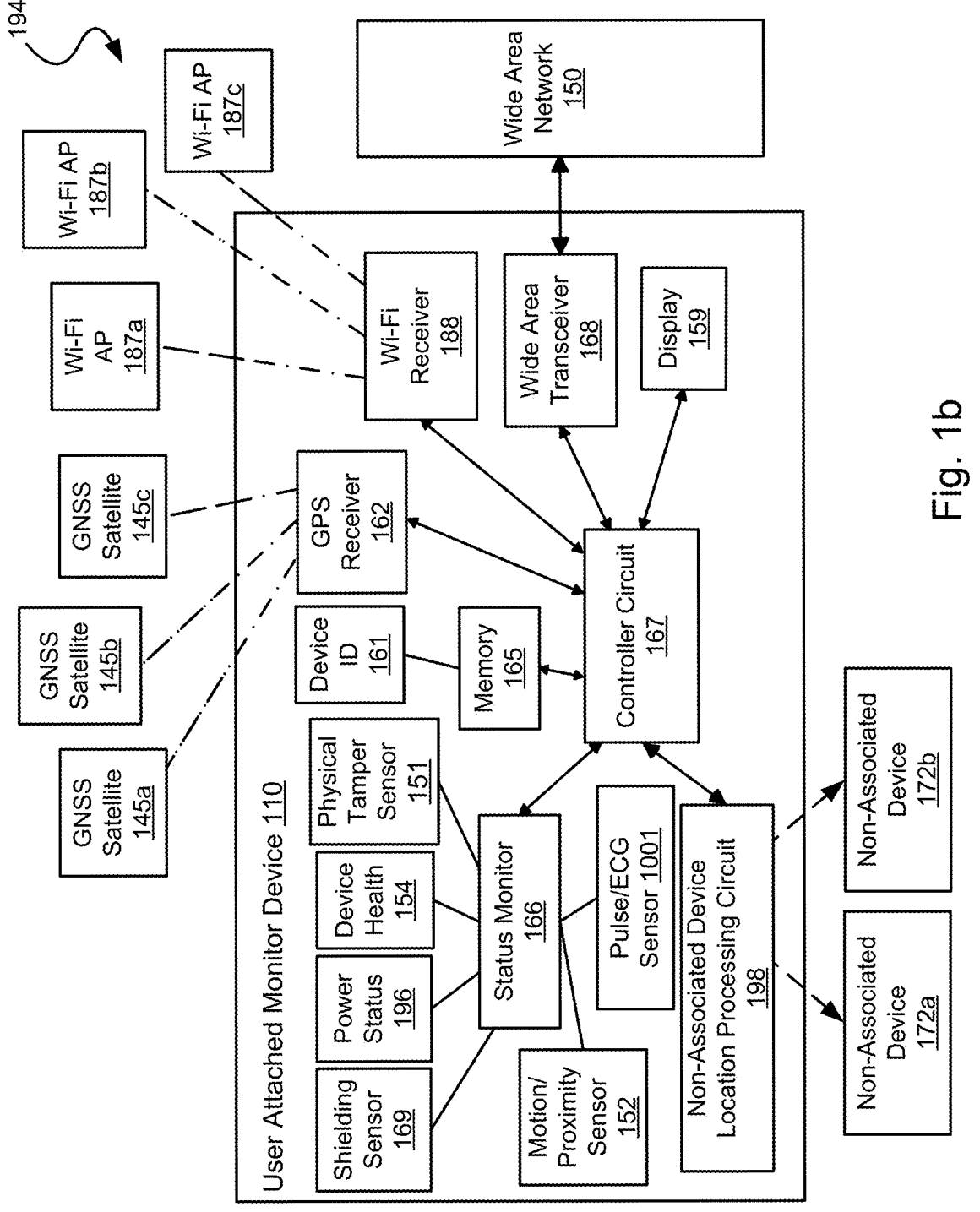

Turning to FIG. 1b, a block diagram 194 of user attached monitor device 110 is shown in accordance with some embodiments. As shown, user attached monitor device 110 includes a device ID 161 that may be maintained in a memory 165, and is thus accessible by a controller circuit 167. Controller circuit 167 interacts with a GPS receiver 162 and memory 165 at times for storing and generating records of successively determined GPS locations. Similarly, controller circuit 167 interacts with a WiFi receiver 188 and memory 165 at times for storing and generating records of successively determined WiFi access point identifications and signal strength. In some cases, memory 165 may include instructions (e.g., software-based or firmware-based instructions) executable by controller circuit 167 to perform and/or enable various functions associated with user attached monitor device 110. As user attached monitor device 110 comes within range of one or more WiFi access points (e.g., a WiFi access point 187a, a WiFi access point 187b, and/or a WiFi access point 187c), WiFi receiver 188 senses the signal provided by the respective WiFi access points, and provides an identification of the respective WiFi access point and a signal strength of the signal received from the WiFi access point to WiFi receiver 188. This information is provided to controller circuit 167 which stores the information to memory 165.

Additionally, user attached monitor device 110 includes a non-associated device location processing circuit 198. Non-associated device location processing circuit 198 is configured to sense that one or more non-associated devices 172 is/are within range of user attached monitor device 110, and to communicate (i.e., transmit) an identification of user attached monitor device 110 to the identified non-associated device. In turn, the non-associated device that received the identification information from user attached monitor device 110 reports the identification received from user attached monitor device 110 and the location of the non-associated device to third-party location reporting system 170. Third-party location reporting system 170 in turn transfers the received identification and location information to a recipient registered with the received identification in the system. In this case, the recipient registered with the received identification in the system is central monitoring station 160. The power requirements of the user attached monitor device 110 for identifying the non-associated device and communicating the identification to the non-associated device are substantially less than determining location based either on WiFi access points 187 or GNSS satellites 145.

Where user attached monitor device 110 is operating in a standard mode, controller circuit 167 causes an update and reporting of the location of user attached monitor device 110 via a wide area transceiver 168 and wide area communication network 150. In some embodiments, wide area transceiver 168 is a cellular telephone transceiver. In some cases, the location data is time stamped. In contrast, where user attached monitor device 110 is within range of a public WiFi access point, reporting the location of user attached monitor device 110 may be done via the public WiFi access point in place of the cellular communication link. In other modes triggered by conditions in user detached monitor device 110, controller circuit 167 causes non-associated device location processing circuit 198 to provide for reporting a proxy for the location of user attached monitor device 110 by transmitting its identification to any non-associated device 172 within range. In such a case, the proxy for the location is the location of the non-associated device 172 that received identification from user attached monitor device 110. Conditions for using the proxy location by communicating the identification information of user attached monitor device 110 are discussed more fully in relation to FIGS. 4-8 below.

Which technologies (e.g., GNSS and/or WiFi) are used to update the location of user attached monitor device 110 may be selected either by default, by programming from central monitor station 160, or based upon conditions detected in user attached monitor device 110 with corresponding predetermined selections. For example, it may be determined whether sufficient battery power as reported by power status 196 remains in user attached monitor device 110 to support a particular position determination technology. Where insufficient power remains, using the proxy location by communicating the identification information of user attached monitor device 110 to a non-associated device 172 may be enabled and other location technologies disabled.

In some cases, a maximum cost of resolving location may be set for user attached monitor device 110. For example, resolving WiFi location data or via a non-associated device may incur a per transaction cost to have a third-party service provider resolve the location information. When a maximum number of resolution requests have been issued, the WiFi position determination technology or the non-associated device approach may be disabled.

Further, it may be determined whether the likelihood that a particular position determination technology will be capable of providing meaningful location information. For example, where user attached monitor device 110 is moved indoors, GPS receiver 162 may be disabled to save power. Alternatively, where the tracking device is traveling at relatively high speeds, WiFi receiver 188 may be disabled. As yet another example, where cellular phone jamming is occurring, support for cell tower triangulation position determination may be disabled. As yet another example, where GPS jamming is occurring, GPS receiver 162 may be disabled. As yet another example, where user attached monitor device 110 is stationary, the lowest cost (from both a monetary and power standpoint) tracking may be enabled while all other technologies are disabled. Which position determination technologies are used may be based upon a zone in which a tracking device is located. Some zones may be rich in WiFi access points and in such zones WiFi technology may be used. Otherwise, another technology such as cell tower triangulation or GPS may be used. Based upon the disclosure provided herein, one of ordinary skill in the art will recognize other scenarios and corresponding combinations of technologies may be best.

Controller circuit 167 of user attached monitor device 110 at times functions in conjunction with wide area transceiver 168 to send and receive data and signals through wide area communication network 150. This link at times is useful for passing information and/or control signals between a central monitoring system 160 and user attached monitor device 110. The information transmitted may include, but is not limited to, location information, measured alcohol information, one or more passive or active impairment tests applied to the monitored individual, and information about the status of user attached monitor device 110. Based on the disclosure provided herein, one of ordinary skill in the art will recognize a variety of information that may be transferred via wide area communication network 150.

Various embodiments of user attached monitor device 110 include a variety of sensors capable of determining the status of user attached monitor device 110, and of the individual to which it is attached. For example, a status monitor 166 may include one or more of the following subcomponents: power status sensor 196 capable of indicating a power status of user attached monitor device 110, and/or a pulse/ECG sensor 1001 operable to sense pulse rate of the monitored individual and an electrocardiogram unique to the monitored individual based upon electrodes (not shown) in contact with the skin of the monitored individual. The power status may be expressed, for example as a percentage of battery life remaining. Based upon the disclosure provided herein, one of ordinary skill in the art will recognize a variety of forms in which power status may be expressed. The pulse rate may be expressed in beats per minute and the ECG may be shown visually via display 159. Based upon the disclosure provided herein, one of ordinary skill in the art will recognize a variety of forms in which pulse rate and/or ECG rate may be expressed.

In addition, user attached monitor device 110 includes a set of shielding sensors 169 that are capable of determining whether user attached monitor device 110 is being shielded from receiving GPS signals and/or if GPS jamming is ongoing, a set of device health indicators 154, a tamper sensor 151 capable of determining whether unauthorized access to user attached monitor device 110 has occurred or whether user attached monitor device 110 has been removed from an associated individual being monitored, and/or a motion/proximity sensor 152 capable of determining whether user attached monitor device 110 is moving and/or whether it is within proximity of an individual associated with user detached monitor device (not shown-see FIG. 3) associated with the monitored individual. In some cases, motion/proximity sensor 152 includes one or more accelerometer sensors and/or vibration gyro sensors that are capable of accurately sensing motion of the monitored individual. In addition, motion/proximity sensor 152 includes sensors capable of determining a proximity of user attached monitor device 110 to a monitored individual to which the device is assigned. This information may be used to assure that the monitored individual is wearing user attached monitor device 110. Based on the disclosure provided herein, one of ordinary skill in the art will recognize a variety of shielding sensors, a variety of device health transducers and indicators, a variety of tamper sensors, various different types of motion sensors, different proximity to human sensors, and various human body physical measurement sensors or transducers that may be incorporated into user attached monitor device 110 according to various different instances and/or embodiments.

In some embodiments, a user input (not shown) may be integrated into a display 159 and allows for a user of user attached monitor device 110 to provide information to user attached monitor device 110. Display 159 is communicatively coupled to controller circuit 167.

Figure 1C:
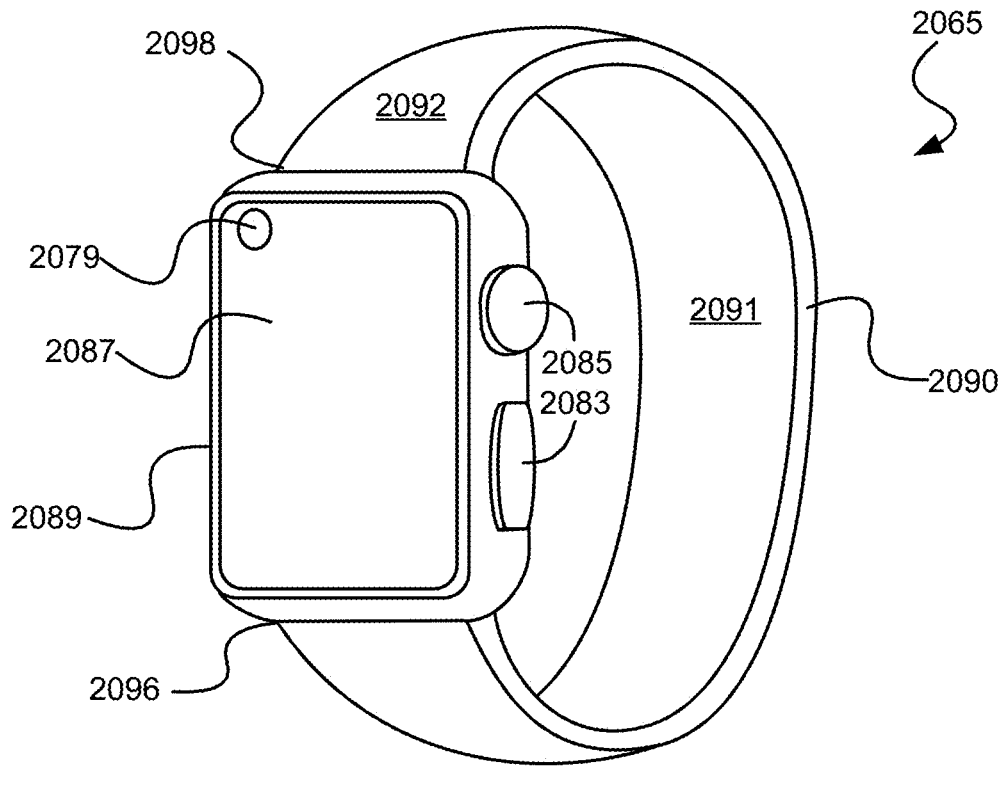

Turning to FIG. 1c, a user attached monitor device 2065 is shown with an example attachment element 2090 connected at opposite ends of user attached monitor device 2065 (i.e., a first end 2096 and a second end 2098). User attached monitor device 2065 is one example implementation of user attached monitor device 110 of FIGS. 1a-1b, user attached monitor device 210 of FIGS. 2*a*-2*b*, or user attached monitor device 310 of FIG. 3. Attachment element 2090 has an outer surface 2092 and an inner surface 2091. Attachment element 2090 is operable to securely attach a user attached monitor device 2065 to a limb of an individual in accordance with some embodiments. In some cases, attachment element 2090 is tailored to attach to a wrist of a monitored individual. In various embodiments, attachment element 2090 includes electrically and/or optically conductive material used to make a conductive connection from first end 2096 to second end 2098 through attachment element 2090 and is used in relation to determining whether user attached monitor device 2065 remains attached and/or has been tampered with. Thus, for example, where attachment element 2090 is cut, the conductive connection is broken indicating a tamper has occurred. While FIG. 1*c* shows a strap as an example attachment element, based upon the disclosure provided herein, one of ordinary skill in the art will recognize other types of attachment elements that may be used in relation to different embodiments. In other embodiments, attachment element 2090 is long enough to attach around the torso of the monitored individual and is sufficiently flexible to allow expansion and contraction of the chest of the monitored individual as they breath. Such expansion and contraction may be used to sense respiration rate of the monitored individual.

User attached monitor device 2065 includes a case 2089 in which various electronic components are maintained. In addition, user attached monitor device 2065 includes a button 2083, a radial dial 2085, a display 2087 (which may be a touchscreen display), and a combination speaker, microphone, and image sensor 2079. Together, user attached monitor device 2065 includes a button 2083, a radial dial 2085, a display 2087, a combination speaker, microphone, and image sensor 2079 provide the user interface for user attached monitor device 2065 and support the functionality of the various sensors discussed above in relation to FIG. 1*b*. Based upon the disclosure provided herein, one of ordinary skill in the art will recognize a variety of inputs and outputs that may be incorporated into user attached monitor device 2065 to provide the functionality discussed herein.

Figure 1D:

Turning to FIG. 1*d*, a user attached monitor device 1100 is shown with an example attachment element 1090 connected at opposite ends of a case 1089. User attached monitor device 1100 is another example implementation of user attached monitor device 110 of FIGS. 1*a*-1*b*, user attached monitor device 210 of FIGS. 2*a*-2*b*, or user attached monitor device 310 of FIG. 3. Attachment element 1090 is configured to securely attach a case 1089 to a limb of an individual in accordance with some embodiments. In various embodiments, attachment element 1090 includes electrically and/or optically conductive material used to make a conductive connection from one side of case 1089 to the opposite side of case 1089 and is used in relation to determining whether user attached monitor device 1100 remains attached and/or has been tampered with. While FIG. 1*d* shows a strap as an example attachment element, based upon the disclosure provided herein, one of ordinary skill in the art will recognize other types of attachment elements that may be used in relation to different embodiments.

Figure 2A:
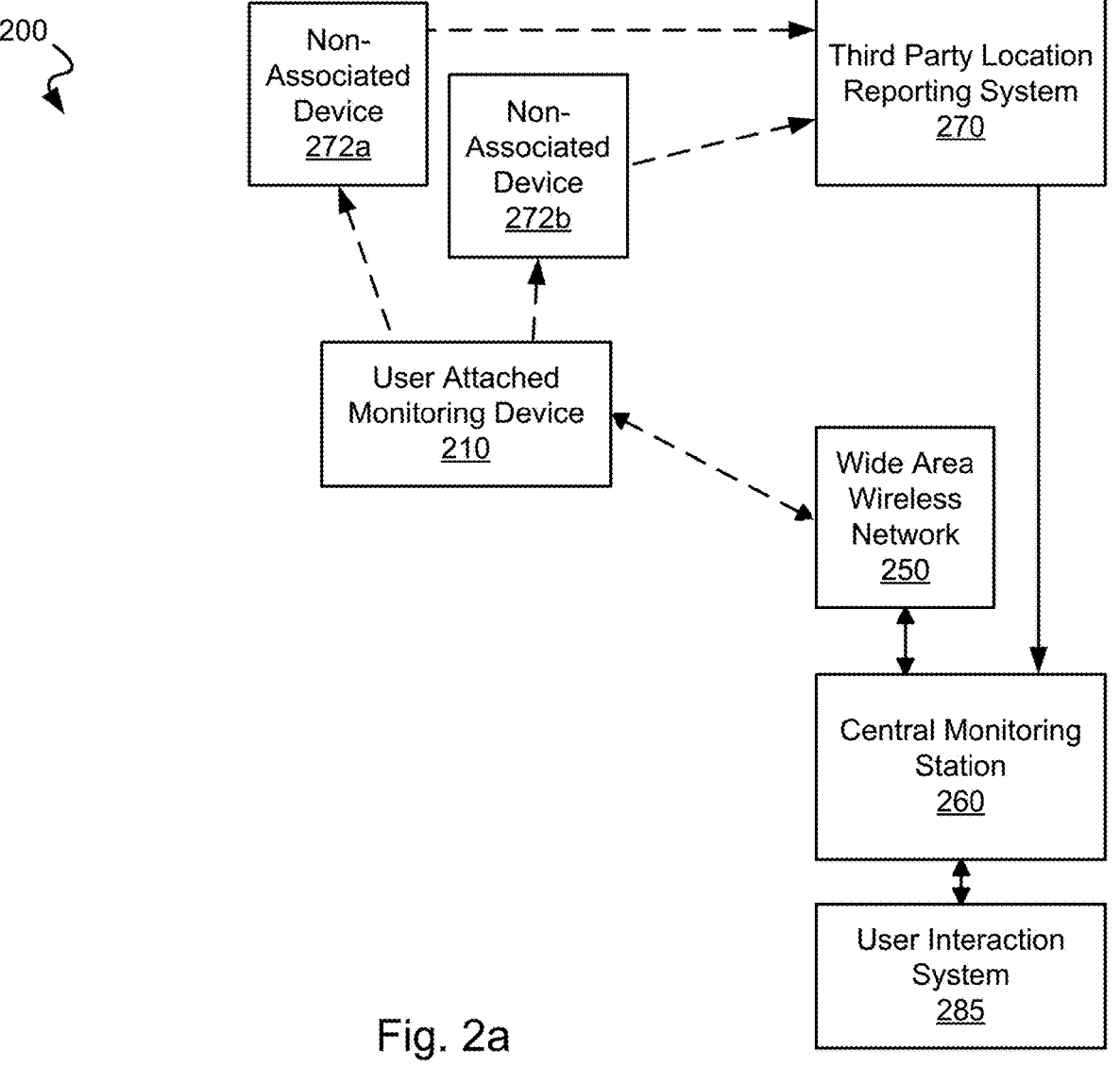
FIGS. 2a-2b are block diagrams illustrating a location monitoring system that includes only non-associated device-based location determination circuitry in accordance with some embodiments.

Turning to FIG. 2*a*, a block diagram of a location monitoring system 200 that includes only non-associated device-based location determination circuitry is shown in accordance with some embodiments. As shown, location monitoring system 200 includes a user attached monitor device 210 that is communicably coupled to a central monitoring station 260 via a wide area wireless network 250 (e.g., cellular telephone network, Internet via a WiFi access point, or the like).

Central monitoring station 260 may be any location, device or system where location data and/or other types of data are received, including by way of non-limiting example: a cellular/smart phone, an email account, a website, a network database, and a memory device. The location data and/or other types of data are stored by central monitoring station 260 and is retrievable by a monitoring individual, such as a parent, guardian, parole officer, court liaison, spouse, friend, or other authorized group or individual. In this manner, the monitoring individual is able to respond appropriately to detected activity of a monitored individual. In some cases, the monitoring individual is able to retrieve the location data and/or other data types via a user interaction system 285 which may be, but is not limited to, a network connected user interface device communicatively coupled via a network to central monitoring station 260 and/or directly to user attached monitor device 210 via wide area wireless network 250.

Central monitoring station 260 may include a server supported website, which may be supported by a server system comprising one or more physical servers, each having a processor, a memory, an operating system, input/output interfaces, and network interfaces, all known in the art, coupled to the network. The server supported website comprises one or more interactive web portals through which the monitor may monitor the location of the monitored individual in accordance with the described embodiments. In particular, the interactive web portals may enable the monitor to retrieve the location and user identification data of one or more monitored individuals, set or modify 'check-in' schedules, and/or set or modify preferences. The interactive web portals are accessible via a personal computing device, such as for example, a home computer, laptop, tablet, and/or smart phone.

In some embodiments, the server supported website comprises a mobile website or mobile application accessible via a software application on a mobile device (e.g. smart phone). The mobile website may be a modified version of the server supported website with limited or additional capabilities suited for mobile location monitoring.

User attached monitor device 210 includes non-associated device-based location determination circuitry that is configured to sense that one or more non-associated devices 272 (e.g., a non-associated device 272*a* and/or a non-associated device 272*b*) is/are within range of user attached monitor device 210, and to communicate (i.e., transmit) an identification of user attached monitor device 210 to the identified non-associated device. In some embodiments, the aforementioned communications are performed via BlueTooth™ or another relatively short-range, low-power communication protocol. Based upon the disclosure provided herein, one of ordinary skill in the art will recognize a variety of protocols that may be used for communications between user attached monitor device 210 and a nearby non-associated device 272.

In turn, the non-associated device that received the identification information from user attached monitor device 210 reports the identification received from user attached monitor device 210 and the location of the non-associated device to a third-party location reporting system 270. Third-party location reporting system 270 in turn transfers the received identification and location information to a recipient registered with the received identification in third-party location reporting system 270. In this case, the recipient registered with the received identification in third-party location reporting system 270 is central monitoring station 260. In such a case, a location of the non-associated device that provided the identification of user attached monitor device 210 to third-party location reporting system 270 is established by central monitoring station 260 as the location of user attached monitor device 210.

Figure 2B:
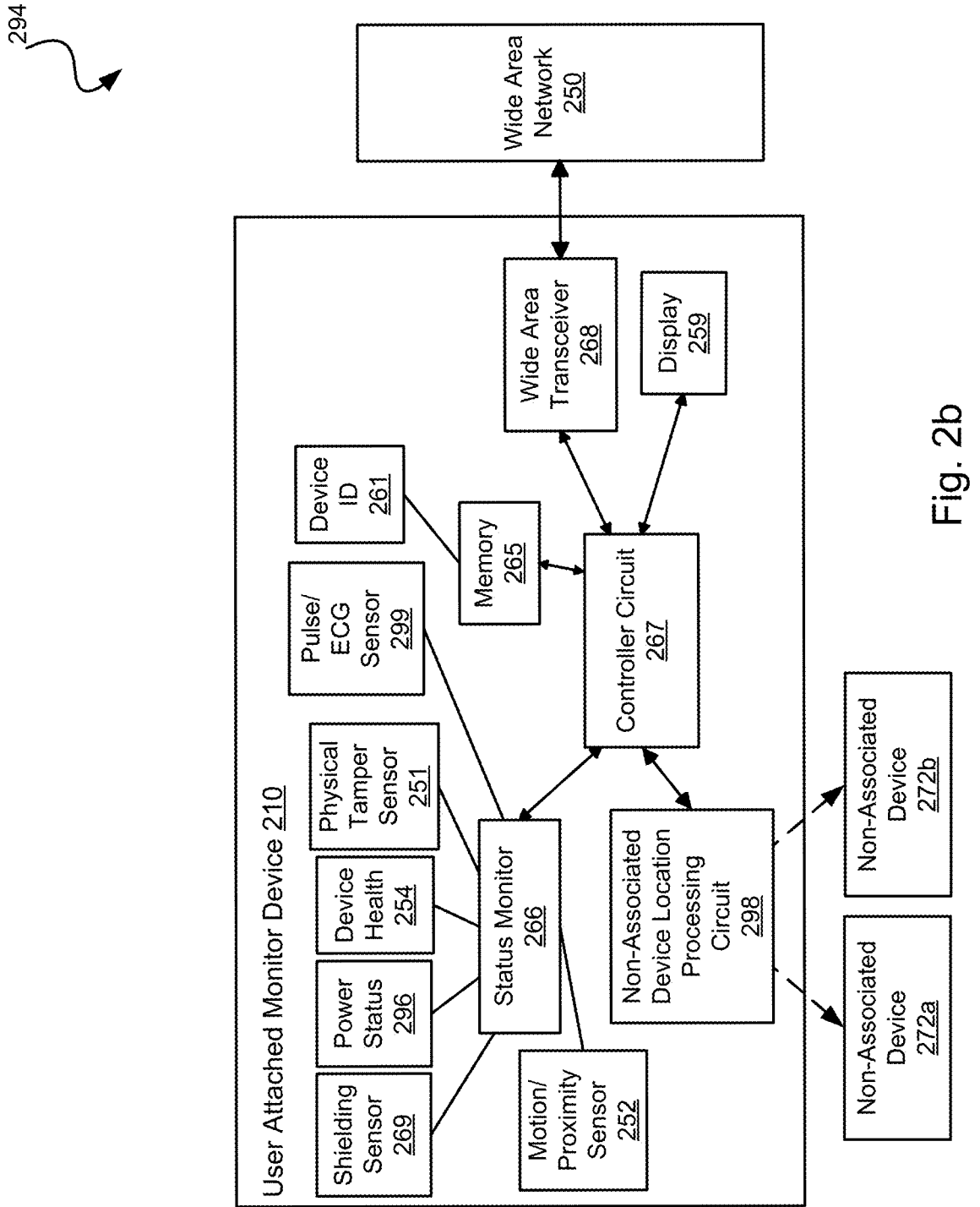

Turning to FIG. 2b, a block diagram 294 of user attached monitor device 210 is shown in accordance with some embodiments. As shown, user attached monitor device 210 includes a device ID 261 that may be maintained in a memory 265, and is thus accessible by a controller circuit 267. In some cases, memory 265 may include non-transient instructions (e.g., software-based or firmware-based instructions) executable by controller circuit 267 to perform and/or enable various functions associated with user attached monitor device 210.

User attached monitor device 210 includes a non-associated device location processing circuit 298. Non-associated device location processing circuit 298 is configured to sense that one or more non-associated devices 272 is/are within range of user attached monitor device 210, and to communicate (i.e., transmit) an identification of user attached monitor device 210 to the identified non-associated device. In turn, the non-associated device that received the identification information from user attached monitor device 210 reports the identification received from user attached monitor device 210 and the location of the non-associated device to third-party location reporting system 270. In turn, third-party location reporting system 270 transfers the received identification and location information to a recipient registered with the received identification in the system. In this case, the recipient registered with the received identification in the system is central monitoring station 260. As discussed above, the non-associated devices 272 may be, but are not limited to, mobile telephones, smart watches, or the like that are accessible to third-party location reporting system 270. In one particular embodiment, the combination of non-associated devices 272 and third-party location reporting system 270 are included in the crowd sourced location system provided by Apple™. Based upon the disclosure provided herein, one of ordinary skill in the art will recognize a variety of devices that may be used as non-associated devices, and a variety of systems that may include both non-associated devices and a third-party reporting system used for identifying the location of devices providing identifications to non-associated devices.

When triggered by particular conditions in user detached monitor device 210, controller circuit 267 causes non-associated device location processing circuit 298 to provide for location of user attached monitor device by transmitting its identification to any non-associated device 272 within range. Such conditions and locating operation is discussed more fully in relation to FIGS. 4-8 below.

Various embodiments of user attached monitor device 210 include a variety of sensors capable of determining the status of user attached monitor device 210, and of the individual associated therewith. For example, a status monitor 266 may include one or more of the following subcomponents: power status sensor 296 capable of indicating a power status of user attached monitor device 210, and/or a pulse/ECG sensor 299 operable to sense pulse rate of the monitored individual and an electrocardiogram unique to the monitored individual based upon electrodes (not shown) in contact with the skin of the monitored individual. The power status may be expressed, for example as a percentage of battery life remaining. Based upon the disclosure provided herein, one of ordinary skill in the art will recognize a variety of forms in which power status may be expressed. The pulse rate may be expressed in beats per minute and the ECG may be shown visually via display 259. Based upon the disclosure provided herein, one of ordinary skill in the art will recognize a variety of forms in which pulse rate and/or ECG rate may be expressed.

In addition, user attached monitor device 210 includes a set of shielding sensors 269 that are capable of determining whether user attached monitor device 210 is being shielded from receiving wireless communications, a set of device health indicators 254, a tamper sensor 251 capable of determining whether unauthorized access to user attached monitor device 210 has occurred or whether user attached monitor device 210 has been removed from an associated individual being monitored, and/or a motion/proximity sensor 252 capable of determining whether user attached monitor device 210 is moving and/or whether it is within proximity of an individual associated with user detached monitor device (not shown-see FIG. 3) associated with the monitored individual. In some cases, motion/proximity sensor 252 includes one or more accelerometer sensors and/or vibration gyro sensors that are capable of accurately sensing motion of the monitored individual. In addition, motion/proximity sensor 252 includes sensors capable of determining a proximity of user attached monitor device 210 to a monitored individual to which the device is assigned. This information may be used to assure that the monitored individual is wearing user attached monitor device 210. Based on the disclosure provided herein, one of ordinary skill in the art will recognize a variety of shielding sensors, a variety of device health transducers and indicators, a variety of tamper sensors, various different types of motion sensors, different proximity to human sensors, and various human body physical measurement sensors or transducers that may be incorporated into user attached monitor device 210 according to various different instances and/or embodiments.

In some embodiments, a user input (not shown) may be integrated into a display 250 and allows for a user of user attached monitor device 210 to provide information to user attached monitor device 210. Display 259 is communicatively coupled to controller circuit 267.

Figure 3:
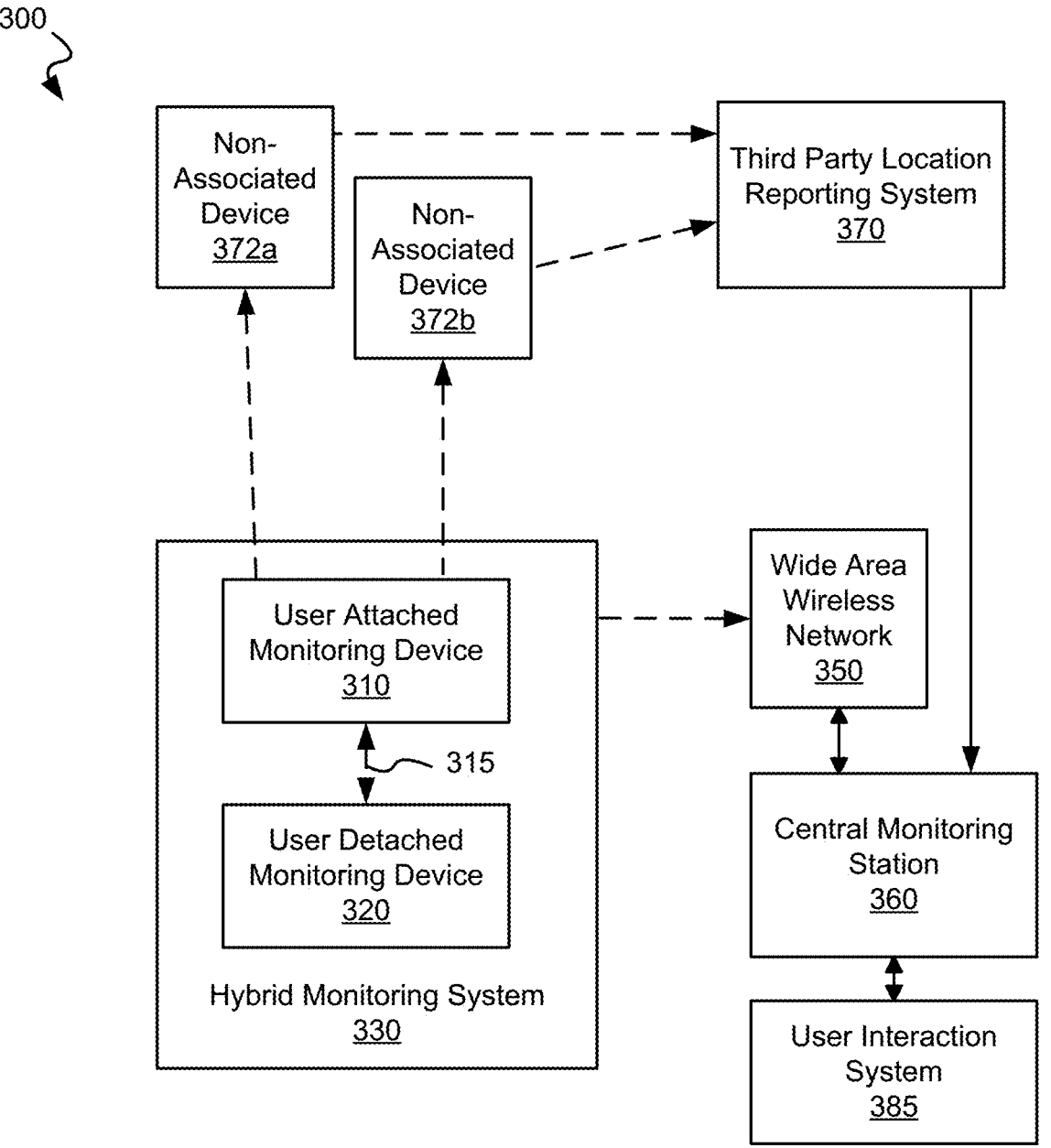
FIG. 3 is a block diagram of a location monitoring system including a hybrid monitoring system capable of establishing location using one or more of WiFi access point-based location determination circuitry, satellite-based location determination circuitry, and/or non-associated device-based location determination circuitry in accordance with various embodiments.

Turning to FIG. 3, a block diagram is shown of a location monitoring system 300 including a hybrid monitoring system 330 capable of establishing location using one or more of WiFi access point-based location determination circuitry, satellite-based location determination circuitry, and/or non-associated device-based location determination circuitry in accordance with various embodiments. Hybrid monitoring system 330 includes both a user attached monitor device 310 and a user detached monitor device 320. User attached monitor device 310 is similar to either user attached monitor device 110 or user attached monitor device 210. Hybrid monitoring system 330 is configured to establish a proxy location using one or more non-associated devices 372 and a third-party location reporting system 370 similar to that discussed above in relation to FIGS. 1-2.

User detached monitor device 320 is portable, and may be any device that is recognized as being used by or assigned to an individual being monitored, but is not physically attached to the individual being monitored by a tamper evident attaching device. User detached monitor device 120 may be, but is not limited to, a cellular or mobile telephone configured to communicate with user attached monitor device 310 via a local communication link 315. In contrast, user attached monitor device 310 is attached to the individual being monitored using a tamper evident attaching device like a strap. User attached monitor device 310 may be, but is not limited to, a tracking device that is attached around the limb of an individual and includes indicators to monitor whether the device has been removed from the individual or otherwise tampered.

Location monitoring system 300 further includes a central monitoring station 360 wirelessly coupled to user attached monitor device 310 and/or user detached monitor device 320 via one or more wide area wireless (e.g., cellular telephone network, Internet via a Wi-Fi access point, or the like) communication networks 350.

User detached monitor device 320 includes a location sensor that senses the location of the device and generates a location data. The location data may comprise one or more of: global positioning system ("GPS") data, Assisted GPS ("A-GPS") data, Advanced Forward Link Trilateration ("AFLT") data, and/or cell tower triangulation data. The aforementioned location data is utilized verify the location of a user associated with user detached monitor device 320 at various points as more fully discussed below. User detached monitor device 320 is considered "ambiguous" because it is not attached to the user in a tamper resistant/evident way, but rather is freely severable from the user and thus could be used by persons other than the target. Various processes discussed herein mitigate the aforementioned ambiguity to yield a reasonable belief that information derived from user detached monitor device 320 corresponds to the target.

The location data and/or other data gathered by user detached monitor device 320 may be wirelessly transmitted to central monitoring station 360 via wide area wireless network. Central monitoring station 360 may be any location, device or system where the location data is received, including by way of non-limiting example: a cellular/smart phone, an email account, a website, a network database, and a memory device. The location data is stored by central monitoring station 360 and is retrievable therefrom by a monitor, such as a parent, guardian, parole officer, court liaison, spouse, friend, or other authorized group or individual. In this manner, monitor is able to respond appropriately to the detected out-of-bounds activity by a user. In some cases, the monitor is able to retrieve the location data via a user interaction system 185 which may be, but is not limited to, a network connected user interface device communicatively coupled to a network to central monitoring station 360 and/or directly to user detached monitor device 320 via wide area wireless network 350.

User detached monitor device 320 may further include a user identification sensor operable to generate user identification data for identifying the user in association with the generation of the location data. The user identification data may comprise one or more of: image data, video data, biometric data (e.g. fingerprint, DNA, retinal scan, etc. data), or any other type of data that may be used to verify the identity of the user at or near the time the location data is generated. And the user identification sensor may comprise one or more of: a camera, microphone, heat sensor, biometric data sensor, or any other type of device capable of sensing/generating the aforementioned types of user identification data.

The user identification data is wirelessly transmitted in association with the location data to central monitoring station 360 via a wireless transmitter communicatively coupled to the user identification sensor. The user identification data is stored in association with the location data by central monitoring station 360 and is retrievable therefrom by a monitor, such as a parent, guardian, parole officer, court liaison, spouse, friend, or other authorized group or individual. The monitor is configured to retrieve the location data via a network connected user interface device communicatively coupled—via the network—to central monitoring station 360 and/or to user detached monitor device 320. The location data may be transmitted to central monitoring station 360 independent of the user identification data, for example, during a periodic check-in with central monitoring system 360.

User detached monitor device 320 may further comprise a memory communicatively coupled to a control unit—which is also communicatively coupled to the location sensor, the identification sensor and the wireless transceiver—for controlling the operations thereof in accordance with the functionalities described herein. The memory may include instructions (e.g., software of firmware based instructions) executable by the control unit to perform and/or enable various functions associated with user detached monitor device 320. As user detached monitor device 320 is portable, each of the components may be located within, immediately adjacent to, or exposed without, a device housing whose dimensions are such that user detached monitor device 320 as a whole may be discretely carried by the user, for example, within a pocket or small purse.

Turning to FIG. 4, a flow diagram 400 shows a method in accordance with some embodiments for utilizing non-associated device-based location in relation to other location methods. Following flow diagram 400, the status of a user attached monitor device is monitored (block 402). This can include monitoring one or more status sensors included in the user attached monitor device. Such status sensors may include, but are not limited to, a power status sensor, a shielding sensor, a device health sensor, a physical tamper sensor, a motion/proximity sensor, and/or a pulse/ECG sensor. Data from one or more of the monitored status sensors is used to determine whether the user attached monitor device has experienced an operational change that would indicate transitioning to location determination based exclusively on non-associated device-based location processing (block 404). One embodiment of implementing the processes of block 404 is discussed below in relation to FIG. 5.

Where it is determined that the user attached monitor device has experienced an operational change that would indicate transitioning to location determination based exclusively on non-associated device-based location processing (block 404), primary location processing using a non-associated device location processing circuit included in the user attached monitor device is performed (block 408). One embodiment showing a method for performing the processes of block 408 is discussed below in relation to FIG. 6.

Alternatively, where it is determined that the user attached monitor device has not experienced an operational change that would indicate transitioning to location determination based exclusively on non-associated device-based location processing (block 404), it is determined whether the user attached monitor device has experienced an operational change that would indicate transitioning to location determination based both upon non-associated device-based location processing and one or more other location processing methods supported by the user attached monitor device (block 406). One embodiment of implementing the processes of block 406 is discussed below in relation to FIG. 7.

Where it is determined that the user attached monitor device has experienced an operational change that would indicate transitioning to location determination based both upon non-associated device-based location processing and one or more other location processing methods supported by the user attached monitor device (block 406), backup location processing using a non-associated device location processing circuit included in the user attached monitor device is performed (block 410). Such backup processing may be selected where location information for a user attached monitor device derived from a WiFi location source has been received over a long period of time. In some cases, such a WiFi location source is a beacon that is deployed at a residence or workplace of an individual to which the user attached monitor device is attached.

When the user attached monitor device comes within range of the beacon which emits a location signal via a WiFi transmission, the user attached monitor device may turn off all GNSS based location circuitry to save power. Some such beacons are plugged in but some operate on battery power, and the beacon has a motion sensor within it. If the motion sensor is tripped, the user attached monitor device re-awakens GNSS location circuitry. However, it may be possible to spoof the WiFi signal or modify the beacon such that it can be moved and yet still report the location where the WiFi source is expected to be. In such a situation it may be desirable to obtain secondary location information using non-associated device processing to confirm the location provided by the WiFi source is accurate. In such a situation, a questionable location information flag may be set causing the user attached monitor device to communicate with one or more non-associated devices within range to perform location processing. In such a case, the location information reported by the non-associated device via a third-party location reporting system can be compared with the location information being reported by the WiFi location circuit of the user attached monitor device to assure that the location of the WiFi source is being reported properly.

Figure 5:
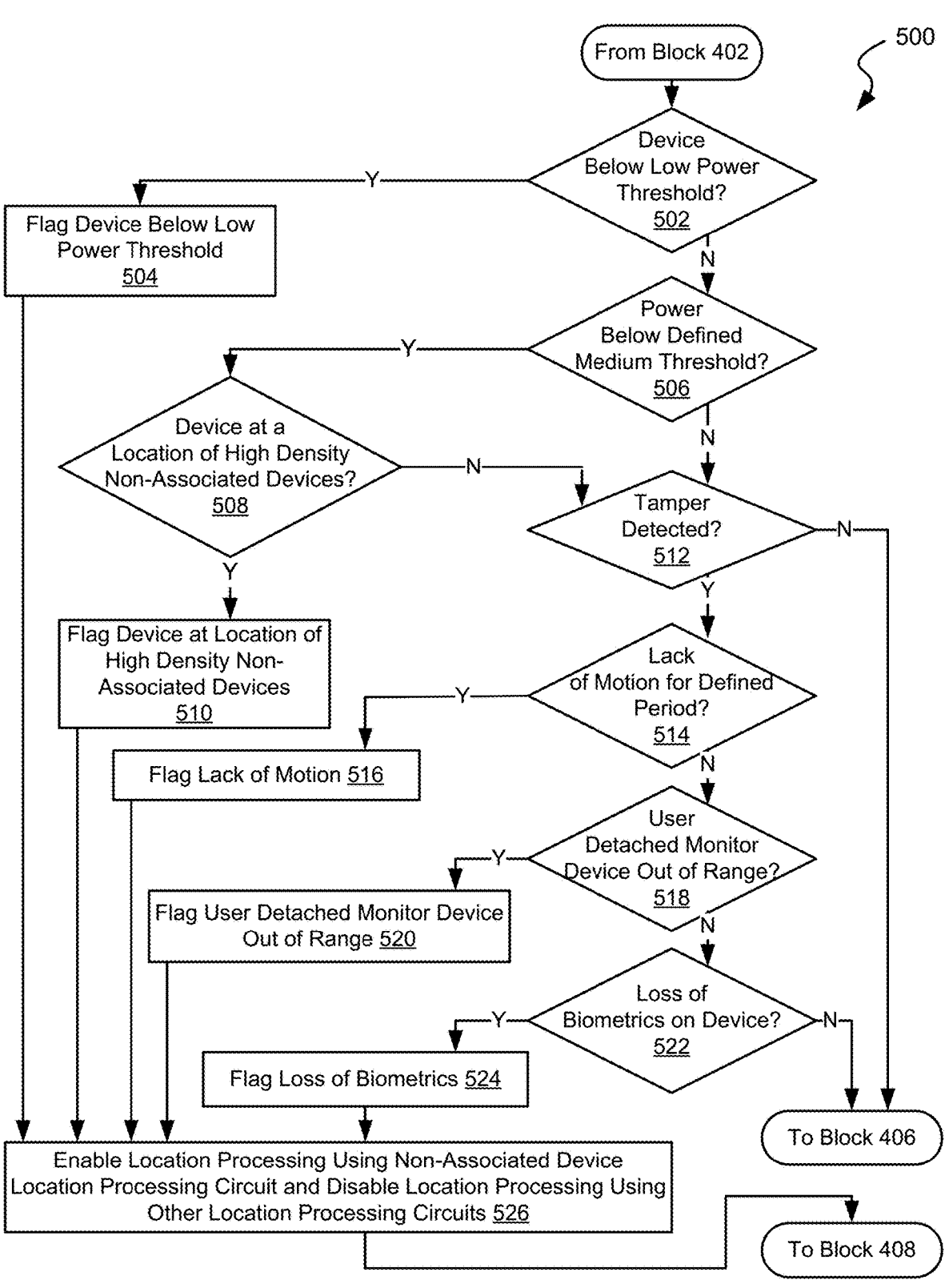
FIGS. 5 and 7 are flow diagrams showing methods in accordance with various embodiments for determining an operational change leading to the use of non-associated device-based location processing.

Turning to FIG. 5, a flow diagram 500 shows a method in accordance with various embodiments for determining an operational change in a user attached monitor device leading to the use of non-associated device-based location processing. Flow diagram 500 begins from block 402 of FIG. 4 and evaluates various monitored data related to the user attached monitor device to determine if a condition has been met to transition the user attached monitor device to using location from non-associated devices as the primary source of location information for the user attached monitor device. Following flow diagram 500, it is determined whether the power source in the user attached monitor device has gone below a low-power threshold (block 502). The low-power threshold may be, for example, a defined percentage of battery life or a time which the device can continue operating on the current charge. This low-power threshold may be user programmable. Based upon the disclosure provided herein, one of ordinary skill in the art will recognize a variety of power thresholds that may be used as the low-power threshold.

Where the power has gone below the low-power threshold (block 502), a below low-power threshold flag is set in the memory of the user attached monitor device (block 504). In addition, location processing using a non-associated device location processing circuit of the user attached monitor device is enabled, and location processing using any of the other location processing circuitry (e.g., WiFi or GPS) is disabled (block 526). In such a situation, the power used by the user attached monitor device is greatly reduced. In addition, the below low-power threshold flag has been set and will remain set until the power of the user attached monitor device is significantly increased as discussed below in relation to FIG. 6, and the processing continues in block 408 of FIG. 4.

Alternatively, where the power has not gone below the low-power threshold (block 502), it is determined whether the power source in the user attached monitor device has gone below a medium power threshold (block 506). The medium power threshold may be, for example a defined percentage of a battery life or a time which the device can continue operating on the current charge. This low-power threshold may be user programmable. Based upon the disclosure provided herein, one of ordinary skill in the art will recognize a variety of power thresholds that may be used as the medium power threshold.

Where the power has gone below the medium power threshold (block 506), it is determined whether the user attached monitor device is currently in a location with a high density of non-associated devices that can be relied upon to transmit location data for the user attached monitor device (block 508). Locations with a high density of non-associated devices may be airports, shopping centers, sports or entertainment venues, or other locations where a large number of people with mobile devices are expected to be. Alternatively, locations with a high density of non-associated devices may be discerned in real time by the user attached monitor device where the user attached monitor device detects at least a defined number of non-associated devices within communication range. Based upon the disclosure provided herein, one of ordinary skill in the art will recognize a variety of approaches for identifying locations with a high density of non-associated devices.

Where it is determined that the power has gone below the medium power threshold (block 506) and the user attached monitor device is operating in a location with a high density of non-associated devices (block 508), a location with a high density of non-associated devices flag is set in the memory of the user attached monitor device (block 510). In addition, location processing using the non-associated device location processing circuit of the user attached monitor device is enabled, and location processing using any of the other location processing circuitry (e.g., WiFi or GPS) is disabled (block 526). In such a situation, the power used by the user attached monitor device is greatly reduced, and the location with a high density of non-associated devices flag has been set and will remain set until either the power of the user attached monitor device is significantly increased or the user attached monitor device moves away from the location with the high density of non-associated devices as discussed below in relation to FIG. 6, and the processing continues in block 408 of FIG. 4.

Alternatively, where it is either determined that the power has not gone below the medium power threshold (block 506) or that the user attached monitor device is not currently in a location with a high density of non-associated devices that can be relied upon to transmit location data for the user attached monitor device (block 508), it is determined whether a tamper has been detected (block 512). A tamper may be any indication that the user attached monitor device has been improperly accessed. Such a tamper may include, but is not limited to, an attempt to remove the user attached monitor device from the monitored individual. As one example, a tamper is indicated when the strap attaching the user attached monitor device to the monitored individual is cut. Based upon the disclosure provided herein, one ordinary skill in the art will recognize a variety of tamper detection circuits that may be used to detect a tamper and a variety of different occurrences where a tamper would be indicated in relation to different embodiments.

Where it is determined that a tamper has been detected (block 512), it is determined whether a lack of motion of the user attached monitor device has occurred (block 514). This lack of motion may be detected, for example, using a motion/proximity sensor included in the user attached monitor device. Detection of a lack of motion after detection of a tamper suggests the possibility that the user attached monitor device has been removed from the monitored individual and discarded. In such a case, a lower power approach to determining the location of the user attached monitor device is important to allow time for the device to be recovered.

Where it is determined that a tamper has been detected (block 512) along with a lack of motion of the user detached monitor device (block 514), a lack of motion flag is set in the memory of the user attached monitor device (block 516). In addition, location processing using the non-associated device location processing circuit of the user attached monitor device is enabled, and location processing using any of the other location processing circuitry (e.g., WiFi or Satellite) is disabled (block 526). In such a situation, the power used by the user attached monitor device is greatly reduced, and the lack of motion flag has been set and will remain set until either the tamper is resolved or motion indicative of attachment of the user attached monitor device to the monitored individual is detected as discussed below in relation to FIG. 6, and the processing continues in block 408 of FIG. 4.

Alternatively, where it is determined that a tamper has been detected (block 512), but motion of the user attached monitor device is continuing (block 514), it is determined whether the user attached monitor device is out of range of a user detached monitor device associated with the monitored individual (block 518). This determination is only made where a hybrid monitoring system is being used. This lack of communication or contact between the user attached monitor device and the user detached monitor device suggests a possibility that the detected tamper related to the user attached monitor device has been removed from the monitored individual, and the monitored individual has carried the user detached monitor device away from the user attached monitor device. In such a case, a lower power approach to determining the location of the user attached monitor device is important to allow time for the device to be recovered.

Where it is determined that a tamper has been detected (block 512) along with a loss of communication with the user detached monitor device (block 518), a user detached monitor device out of range flag is set in the memory of the user attached monitor device (block 520). In addition, location processing using the non-associated device location processing circuit of the user attached monitor device is enabled, and location processing using any of the other location processing circuitry (e.g., WiFi or Satellite) is disabled (block 526). In such a situation, the power used by the user attached monitor device is greatly reduced, and the user detached monitor device out of range flag has been set and will remain set until either the tamper is resolved or the user detached monitor device again starts communicating with the user attached monitor device as discussed below in relation to FIG. 6, and the processing continues in block 408 of FIG. 4.

Alternatively, where it is determined that a tamper has been detected (block 512), and the user detached monitor device remains in range of the user attached monitor device (block 518), it is determined whether the biometrics of the monitored individual are still registering with the user attached monitor device (block 522). Such biometrics may include, but are not limited to, pulse and/or ECG of the monitored individual. This lack of biometrics may be detected, for example, using a pulse/ECG sensor included in the user attached monitor device. Detection of a lack of biometrics after detection of a tamper suggests the possibility that the user attached monitor device has been removed from the monitored individual and discarded. In such a case, a lower power approach to determining the location of the user attached monitor device is important to allow time for the device to be recovered.

Where it is determined that a tamper has been detected (block 512) along with a loss of biometrics (block 522), a loss of biometrics flag is set in the memory of the user attached monitor device (block 524). In addition, location processing using the non-associated device location processing circuit of the user attached monitor device is enabled, and location processing using any of the other location processing circuitry (e.g., WiFi or Satellite) is disabled (block 526). In such a situation, the power used by the user attached monitor device is greatly reduced, and the loss of biometrics flag has been set and will remain set until either the tamper is resolved or the biometrics are again sensed by the user attached monitor device as discussed below in relation to FIG. 6, and the processing continues in block 408 of FIG. 4. Where a tamper has not been detected (block 512) or none of the additional conditions are met (blocks 514, 518, 522), processing returns to block 406 of FIG. 4.

Figure 6:
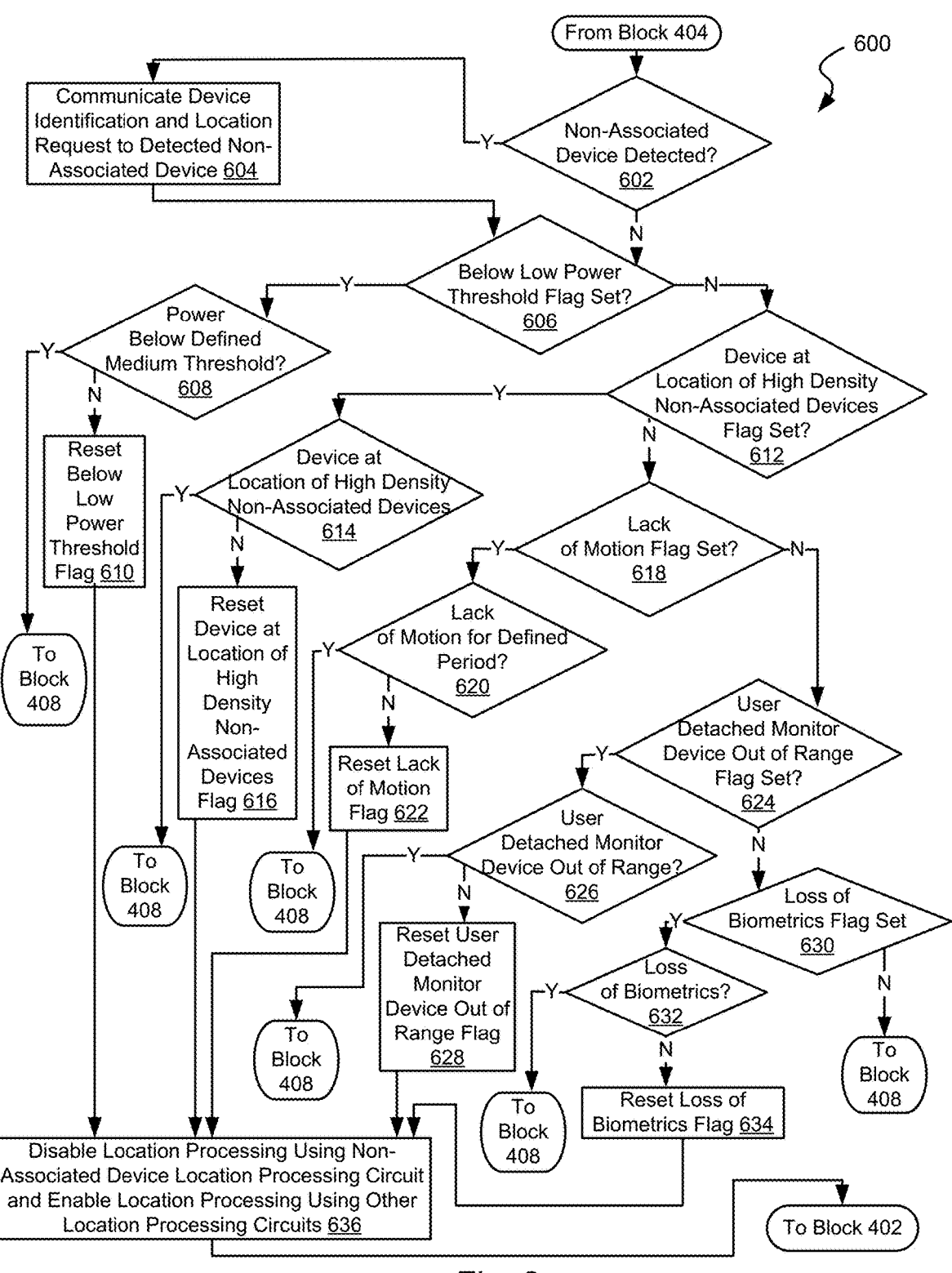
FIGS. 6 and 8 are flow diagrams showing methods in accordance with some embodiments for performing non-associated device-based location processing.

Turning to FIG. 6, a flow diagram 600 shows a method in accordance with various embodiments for performing non-associated device-based location processing. Flow diagram 600 begins from block 404 of FIG. 4 and performs primary location processing using non-associated device location processing circuitry of the user attached monitor device. Following flow diagram 600, it is determined whether a non-associated device has been detected (block 602). A low-power communication protocol such as, for example, BlueTooth™ may be used by a non-associated device location processing circuit of the user attached monitor device to ping for any non-associated devices within communication range. Where a non-associated device is within communication range, the non-associated device location processing circuit indicates detection of a non-associated device.

Where a non-associated device is detected (block 602), the device identification of the user attached monitor device is communicated to the identified non-associated device with, in some cases, a request for the non-associated device to forward the device identification along with the location of the non-associated device to a third-party location reporting system (block 604). In one embodiment, the non-associated devices are configured to provide tracking information via a third-party location reporting system included as part of the crowd sourced location system provided by Apple™.

It is determined whether the below low-power threshold flag is set (block 606). This flag is set whenever the reason for communicating location information via the non-associated devices was triggered due to a low-power condition in the user attached monitor device as discussed above in relation to block 504 of FIG. 5. Where the below low-power threshold flag is set (block 606), it is determined whether the low-power condition of the user attached monitor device still exists or whether the user attached monitor device has been recharged (block 608).

Where the low-power condition no longer exists (block 608), the below low-power threshold flag is reset (block 610), and the location processing using the non-associated device location processing circuit is disabled and location processing using one or more other location processing circuits in the user attached monitor device are re-enabled (block 636). Said another way, the user attached monitor device is returned to its pre-power loss operational status. With the below low-power threshold flag reset (block 610) and the operational status of the user attached monitor device returned (block 636), the process returns to block 402 of FIG. 4. Alternatively, where the low-power condition still exists (block 608), the processing returns to block 408 of FIG. 4 where use of the non-associated devices for location continues.

Alternatively, where the below low-power threshold flag is not set (block 606), it is determined whether the high density of non-associated devices flag is set in the memory of the user attached monitor device (block 612). This flag is set whenever the reason for communicating location information via the non-associated devices was triggered due to a high density of non-associated device as discussed above in relation to block 510 of FIG. 5. Where the high density of non-associated devices flag is set (block 612), it is determined whether the user attached monitor device is still operating in an area that has a high density of non-associated devices (block 614).

Where the high density of non-associated devices no longer exists (block 614), the high density of non-associated devices flag is reset (block 616), and the location processing using the non-associated device location processing circuit is disabled and location processing using one or more other location processing circuits in the user attached monitor device are re-enabled (block 636). Said another way, the user attached monitor device is returned to its pre-power loss operational status. With the high density of non-associated devices flag reset (block 610) and the operational status of the user attached monitor device returned (block 636), the process returns to block 402 of FIG. 4. Alternatively, where the high density of non-associated devices condition still exists (block 614), the processing returns to block 408 of FIG. 4 where use of the non-associated devices for location continues.

Alternatively, where the high density of non-associated devices flag is not set (block 612), it is determined whether the lack of motion flag is set in the memory of the user attached monitor device (block 618). This flag is set whenever the reason for communicating location information via the non-associated devices was triggered due to a lack of motion of the user attached monitor device as discussed above in relation to block 516 of FIG. 5. Where the lack of motion flag is set (block 618), it is determined whether the user attached monitor device is still not moving (block 620).

Where new motion has been detected in the user attached monitor device (block 620), the lack of motion flag is reset (block 622), and the location processing using the non-associated device location processing circuit is disabled and location processing using one or more other location processing circuits in the user attached monitor device are re-enabled (block 636). Said another way, the user attached monitor device is returned to its pre-power loss operational status. With the lack of motion flag reset (block 622) and the operational status of the user attached monitor device returned (block 636), the process returns to block 402 of FIG. 4. Alternatively, where the lack of motion condition still exists (block 620), the processing returns to block 408 of FIG. 4 where use of the non-associated devices for location continues.

Alternatively, where the lack of motion flag is not set (block 618), it is determined whether the user detached monitor device out of range flag is set in the memory of the user attached monitor device (block 6624). This flag is set whenever the reason for communicating location information via the non-associated devices was triggered due to a lack of communication with the user detached monitor device associated with the monitored individual as discussed above in relation to block 520 of FIG. 5. Where the user detached monitor device out of range flag is set (block 624), it is determined whether the user attached monitor device is still out of range of the user detached monitor device (block 626).

Where new communication with the user detached monitor device has been established (block 626), the user detached monitor device out of range flag is reset (block 628), and the location processing using the non-associated device location processing circuit is disabled and location processing using one or more other location processing circuits in the user attached monitor device are re-enabled (block 636). Said another way, the user attached monitor device is returned to its pre-power loss operational status. With the user detached monitor device out of range flag reset (block 628) and the operational status of the user attached monitor device returned (block 636), the process returns to block 402 of FIG. 4. Alternatively, where the user detached monitor device out of range condition still exists (block 626), the processing returns to block 408 of FIG. 4 where use of the non-associated devices for location continues.

Alternatively, where the user detached monitor device out of range flag is not set (block 624), it is determined whether the loss of biometrics flag is set in the memory of the user attached monitor device (block 630). This flag is set whenever the reason for communicating location information via the non-associated devices was triggered due to a lack of biometrics sensed by the user attached monitor device as discussed above in relation to block 524 of FIG. 5. Where the loss of biometrics flag is set (block 630), it is determined whether the loss of biometrics condition continues (block 632).

Where new biometrics are sensed by the user attached monitor device (block 632), the loss of biometrics flag is reset (block 634), and the location processing using the non-associated device location processing circuit is disabled and location processing using one or more other location processing circuits in the user attached monitor device are re-enabled (block 636). Said another way, the user attached monitor device is returned to its pre-power loss operational status. With the loss of biometrics flag reset (block 634) and the operational status of the user attached monitor device returned (block 636), the process returns to block 402 of FIG. 4. Alternatively, where the loss of biometrics condition continues (block 634), the processing returns to block 408 of FIG. 4 where use of the non-associated devices for location continues.

Figure 7:
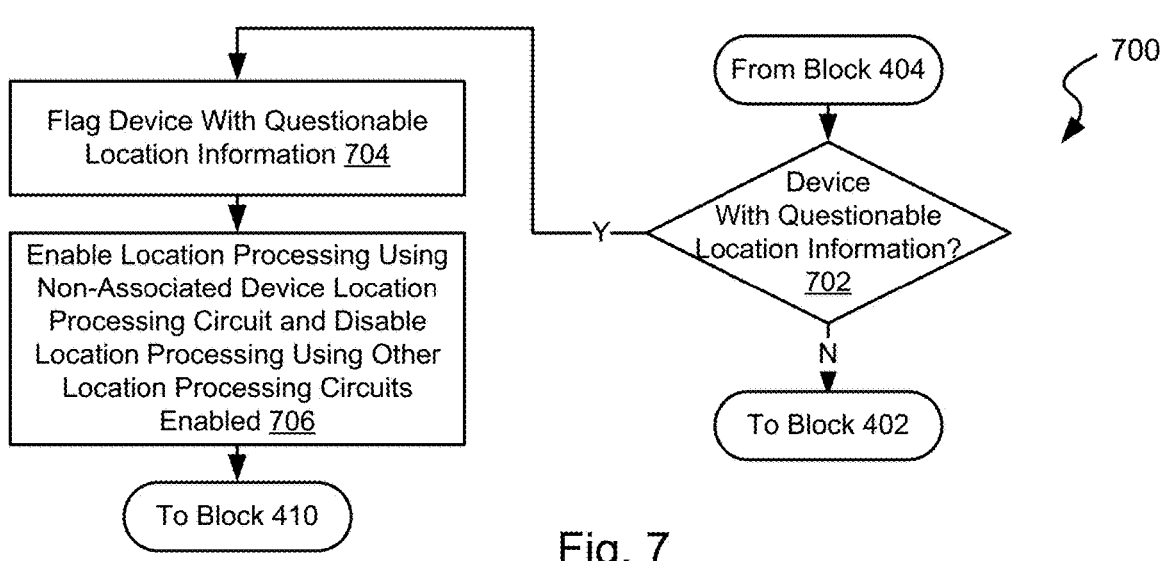

Turning to FIG. 7, a flow diagram 700 shows another method in accordance with various embodiments for determining an operational change leading to the use of non-associated device-based location processing. Flow diagram 700 begins from block 404 of FIG. 4 and evaluates various monitored data related to the user attached monitor device to determine if a condition has been met to transition the user attached monitor device to using location from non-associated devices as the exclusive source of location information for the user attached monitor device. Following flow diagram 700, it is determined whether one or more location circuits of the user attached monitor device is providing questionable location information (block 702). Location information from the user attached monitor device may be considered questionable for any of a number of reasons including, without limitation, successively reported location points indicating that the user attached monitor device is moving faster than is possible, a reported location point that is unlikely due to one or more reasons, or location information being reported when the location of the user attached monitor device is at a location where it is difficult to get accurate location information (e.g., in a building). Based upon the disclosure provided herein, one of ordinary skill in the art will recognize a variety of conditions which would cause the location information reported by the user attached monitor device to be considered questionable.

Where the location information from the user attached monitor device is considered questionable (block 702), a questionable location information flag is set in the memory of the user attached monitor device (block 704). In addition, location processing using a non-associated device location processing circuit of the user attached monitor device is enabled at the same time that location processing using any of the other location processing circuitry (e.g., WiFi or Satellite) is disabled (block 706). The processing then continues with block 410 of FIG. 4. Alternatively, where the location information from the user attached monitor device is not considered questionable (block 702), processing returns to block 402 of FIG. 4.

Figure 8:
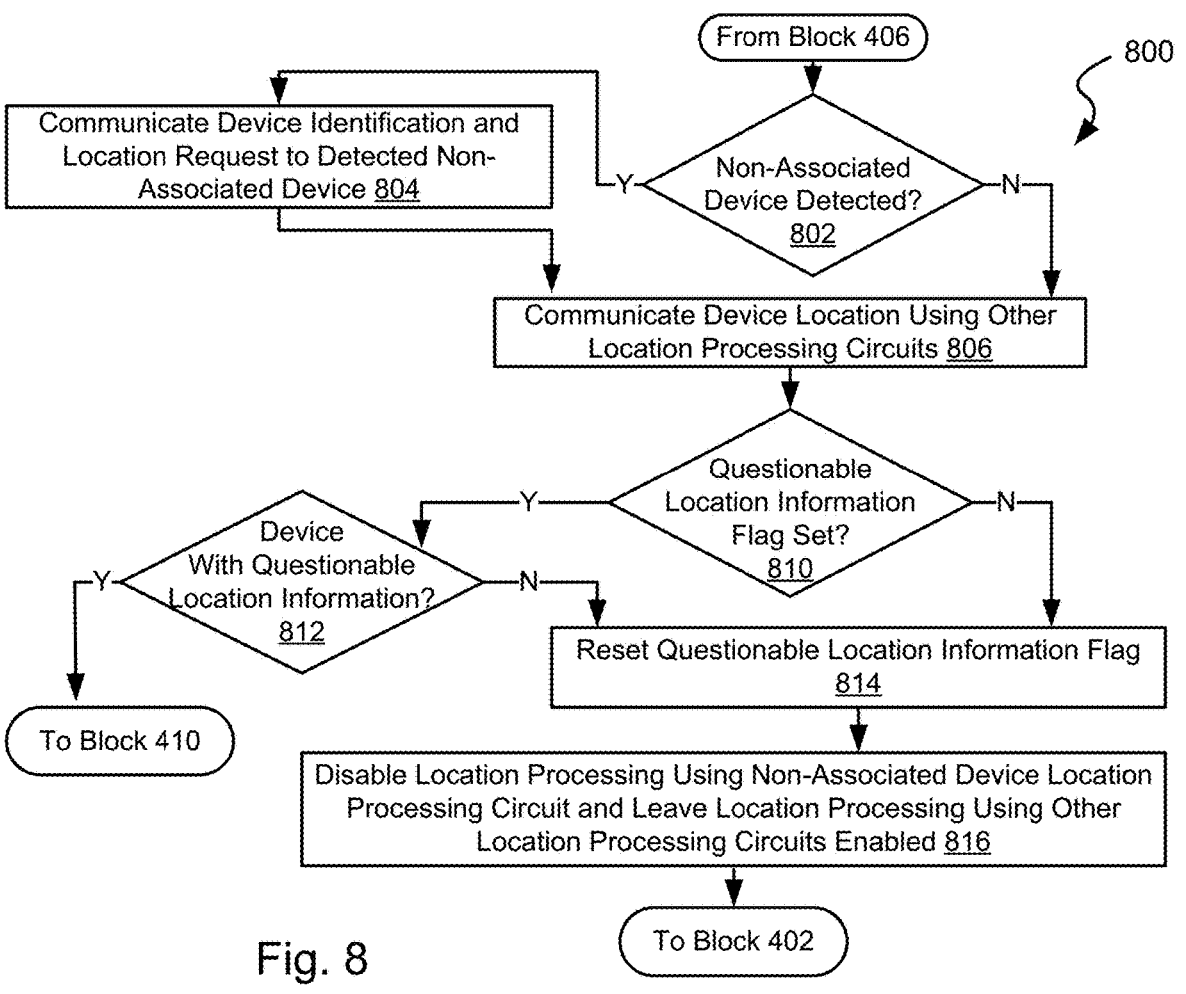

Turning to FIG. 8, a flow diagram 800 shows another method in accordance with various embodiments for determining an operational change leading to the use of non-associated device-based location processing. Flow diagram 800 begins from block 406 of FIG. 4 and determines if a non-associated device is within communication range of a user attached monitor device (block 802). Where a non-associated device is within communication range of a user attached monitor device (block 802), user attached monitor device communicates its identification and a location request to the non-associated device (block 804). In addition, device location is communicated to a central monitoring system using one of the other location circuits (e.g., WiFi or GPS) available in the user attached monitor device (block 806).

It is determined whether a questionable location information flag has been set (block 810). Where a questionable location information flag has been set (block 810), it is determined whether the user attached monitor device is returning questionable location information (block 812). Where either the user attached monitor device is not returning questionable location information (block 812) or the questionable location information flag is not set (block 810), the questionable location information flag is reset (block 814). At this juncture, location processing using non-associated device location processing is disabled and location processing using location circuitry in the user attached monitor device remains enabled (block 816). Processing returns to block 402 of FIG. 4.

Figure 9A:
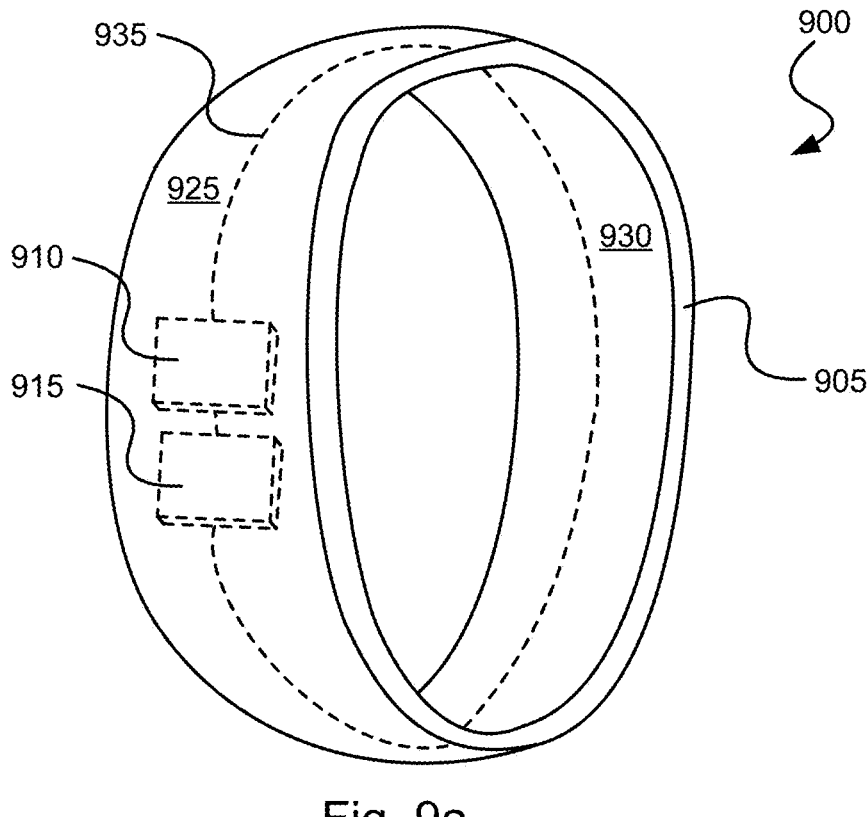
FIGS. 9a-9b depict a simplified user attached monitor device operating in a location monitoring system in accordance with various embodiments.
Figure 9B:
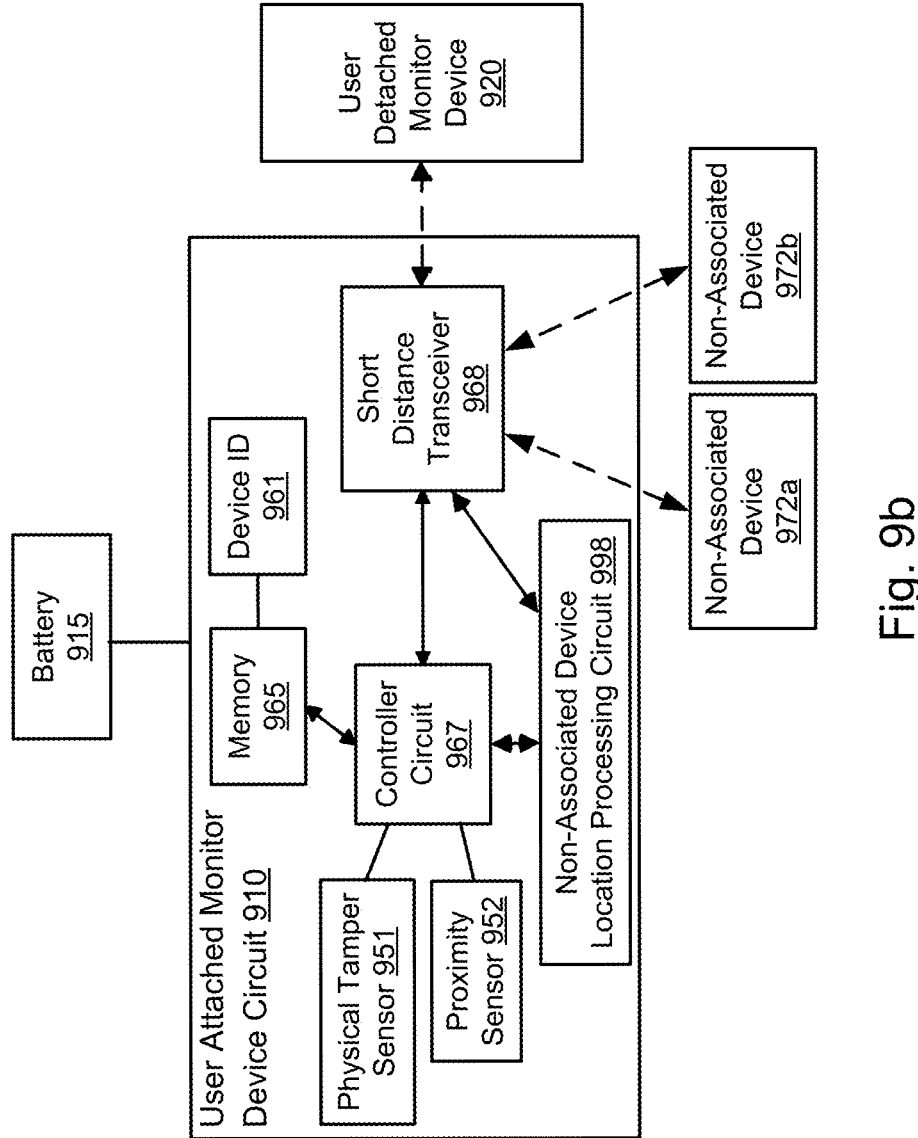

Turning to FIGS. 9a-9b, a simplified user attached monitor device 900 is shown in accordance with some embodiments. Referring specifically to FIG. 9a, user attached monitor device 900 includes a band 905 having an outer surface 925 and an inner surface 930. A battery 915 and a user attached monitor device circuit 910 are embedded in band 905. In some embodiments, user attached monitor device circuit 910 is a low power circuit able to operate off of the power of battery 915 for several months without requiring a recharge. When battery 915 is depleted, user attached monitor device 900 can be removed from a limb of a monitored individual, flags in user attached monitor device circuit 910 can be reset using a wireless interface, and battery 915 can be recharged using contactless charging. User attached monitor device 900 is another example implementation of user attached monitor device 310 of FIG. 3.

Band 905 is operable to securely attach to a limb of an individual in accordance with some embodiments. In some cases, band 905 is tailored to attach to a wrist of a monitored individual. In various embodiments, band 905 includes an electrically and/or optically conductive material 935 used to make a conductive connection from through band 905 to user attached monitor device circuit 910. A signal may be periodically or continuously sent by user attached monitor device circuit 910 through electrically and/or optically conductive material 935 such that if electrically and/or optically conductive material 935 is ever broken user attached monitor device circuit 910 can sense the break and indicate a tamper error. While FIG. 9a shows a band as an example attachment element, based upon the disclosure provided herein, one of ordinary skill in the art will recognize other types of attachment elements that may be used in relation to different embodiments. In other embodiments, band 905 may be replaced by an attachment element that is long enough to attach around the torso of the monitored individual and is sufficiently flexible to allow expansion and contraction of the chest of the monitored individual as they breath. Such expansion and contraction may be used to sense respiration rate of the monitored individual where user attached monitor device circuit 910 is modified to include this additional functionality.

Turning to FIG. 9b, a block diagram of user attached monitor device circuit 910 is shown in accordance with some embodiments. As shown, user attached monitor device circuit 910 includes a device ID 961 that may be maintained in a memory 965 and is thus accessible by a controller circuit 967. Controller circuit 967 may be any circuit capable of causing user attached monitor device 900 to perform its desired functions. In some embodiments, the functions of user attached monitor device circuit 910 include those discussed below in relation to FIG. 10a below. In addition to controlling operation of user attached monitor device 900, controller circuit 967 may receive commands via short distance transceiver 968. Some such commands may reset a previously set removal flag in memory 965, reset a previously set tamper flag in memory 965, and/or reset a connection timer to a first-time value in memory 965. In various embodiments, controller circuit 967 includes a computer processor and memory 965 may include instructions (e.g., software-based or firmware-based instructions) executable by controller circuit 967 to perform and/or enable various functions associated with user attached monitor device 900. Controller circuit 967 interacts with memory 965, a short distance transceiver 968, a non-associated device location processing circuit 998, a tamper sensor 951, and a proximity sensor 952 to perform the various functions of user attached monitor device circuit 910.

Short distance transceiver 968 may be any transceiver circuit capable of establishing wireless communications with a paired device (e.g., a user detached monitor device 920) that is within a defined distance from user attached monitor device circuit 910. In some embodiments, short distance transceiver 968 is configured to support BlueTooth™ communications with either user attached monitor device 920 that is associated with the monitored individual, or with one or more non-associated devices 972 (e.g., non-associated device 972a and/or non-associated device 972b). In some embodiments, user attached monitor device 920 is a mobile phone associated with the monitored individual that is capable of performing the functions discussed below in relation to FIG. 10b. The distance at which the BlueTooth™ communications may be accomplished may be at an expected distance. In some cases, the expected distance may be one distance when one operational status is indicated by user attached monitor device circuit 910, and another distance when another operational status is indicated by user attached monitor device circuit 910. Thus, the expected distance at which short distance transceiver 968 may operate may either be fixed or vary based upon an operational status.

In some embodiments, user attached monitor device circuit 910 includes a received signal strength (RSSI) circuit (not shown) as is known in the art. In such embodiments, the RSSI circuit may be configured to detect a signal at the same frequency used by short distance transceiver 968 and with a higher power (i.e., RSSI) than expected. In such embodiments, the user attached monitor device circuit 910 may set a flag indicating the possibility of jamming.

In some embodiments, the distance at which communications may be supported by user attached monitor device circuit 910 and another device varies depending upon whether user attached monitor device circuit 910 detects that band 905 has been removed from the monitored individual. In some embodiments, the distance at which communications may be supported by user attached monitor device circuit 910 with one or more of user attached monitor device 920 and/or non-associated devices 972 is approximately ten (10) meters when either a removal flag or a tamper flag has been set in user attached monitor device circuit 910, and approximately two (2) meters when neither the removal flag nor the tamper flag has been set in user attached monitor device circuit 910. Such removal and tamper flags may be set and reset by user attached monitor device circuit 910 and stored to memory 965 as more fully discussed below in relation to FIG. 10a. Based upon the disclosure provided herein, one of ordinary skill in the art will recognize other distances that may be supported in relation to different embodiments.

Non-associated device location processing circuit 998 is configured to sense that one or more non-associated devices 972 is/are within range of user attached monitor device circuit 910, and to communicate (i.e., transmit) device identification 961 of user attached monitor device 900 to the identified non-associated device. In turn, the non-associated device that received the identification information from user attached monitor device 900 reports the identification received from user attached monitor device 900 and the location of the non-associated device to a third-party location reporting system (e.g., third-party location reporting system 170 discussed above in relation to FIG. 1a). The third-party location reporting system in turn transfers the received identification and location information to a recipient registered with the received identification in the system. In this case, the recipient registered with the received identification in the system may be a central monitoring station (e.g., central monitoring station 160 discussed above in relation to FIG. 1a). As suggested above, in some embodiments the power requirements of the user attached monitor device circuit 910 for identifying the non-associated device and communicating the identification to the non-associated device may be the same as that required to establish communication with user detached monitor device 920. In other embodiments, the power requirements of the user attached monitor circuit 910 for identifying the non-associated device and communicating the identification to the non-associated device may be greater than that required to establish communication with user detached monitor device 920. The different power requirements may be used to support a larger communication distance between user attached monitor device circuit 910 and non-associated device 972 than the communication distance supported between user attached monitor device circuit 910 and user detached monitor device 920.

Battery 915 may be any mobile source of electrical energy known in the art. In some embodiments, battery 915 is a rechargeable lithium-ion battery. Based upon the disclosure provided herein, one of ordinary skill in the art will recognize a variety of battery types that may be used in relation to different embodiments.

Tamper sensor 951 is capable of determining whether user attached monitor device 900 has been removed from an associated individual being monitored. In some embodiments, tamper sensor 951 is a continuity sensor that generates an electrical or optical signal that is transmitted in a loop around band 905 by electrically and/or optically conductive material 935. Where the transmitted signal does not return, it is an indication that band 905 has been broken and user attached monitor device 900 removed from the monitored individual. When this is detected, tamper sensor 951 provides an indication to controller circuit 967 that sets a tamper flag in memory 965. Based upon the disclosure provided herein, one of ordinary skill in the art will recognize other types of tamper sensors that may be used in relation to different embodiments.

Proximity sensor 952 is capable of determining whether user attached monitor device 900 is within proximity of the monitored individual. Proximity sensor 952 may be any sensor known in the art for discerning a proximity to an expected object. Such proximity sensors include, but are not limited to, a light-based or electromagnetic field-based proximity sensor. A light-based proximity sensor may include a light emitting diode that generates a light output and senses any reflected light output. Thus, when user attached monitor device 900 is attached around the wrist of a monitored individual some light will reflect off of the wrist and be detected. Where no light is detected, it is an indication that user attached monitor device 900 has been removed from the wrist of the monitored individual. An electromagnetic field-based proximity sensor may include a circuit generating a small electromagnetic field. When user attached monitor device 900 is attached around the wrist of a monitored individual, some interference with the electromagnetic field will occur indicating that user attached monitor device 900 is on the wrist. In contrast, where the interference stops or changes, it indicates that user attached monitor device 900 may have been removed from the wrist of the monitored individual. Where a lack of proximity is identified by proximity sensor 952, it is indicated to controller circuit 967 that sets a removal flag in memory 965. Based upon the disclosure provided herein, one of ordinary skill in the art will recognize a variety of proximity sensors that may be used in relation to different embodiments.

Figure 10A:
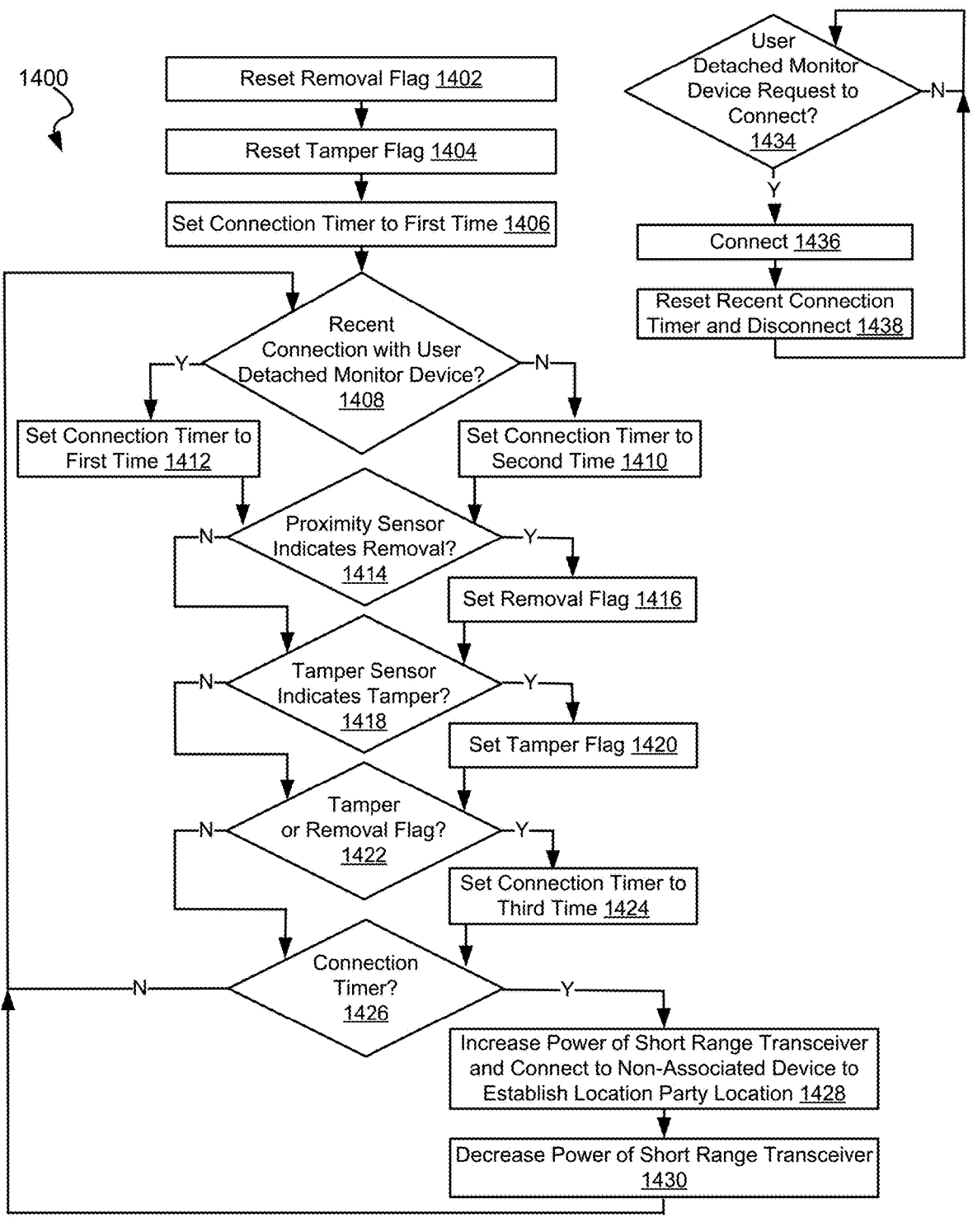
FIGS. 10a-10c are flow diagrams showing a method in accordance with various embodiments for monitoring the veracity of location data using a combination of data from a user attached monitor device, a user detached monitor device, and/or a central monitoring station.

Turning to FIG. 10a, a flow diagram 1400 shows a method in accordance with some embodiments for operating a user attached monitor device. Following flow diagram 1400, a removal flag is reset (block 1402), a tamper flag is reset (block 1404), and a connection timer is set to a first time (block 1406). This may be done by a user detached monitor device or another suitable device wirelessly connecting to the user attached monitor device and communicating a setup command. In response to receiving the setup command, a controller circuit of the user attached monitor device causes each of the resets to occur. The removal flag is set whenever there is an indication internal to the user attached monitor device that the user attached monitor device has been removed from a monitored individual. This removal flag may be set, for example, based upon a proximity sensor in the user attached monitor device. The tamper flag is set whenever there is an indication internal to the user attached monitor device that the user attached monitor device has tampered with. This tamper flag may be set, for example, based upon a tamper sensor in the user attached monitor device.

A connection timer is implemented by a controller circuit in the user attached monitor device, and controls when attempts to communicate with non-associated devices are made. Similar to that discussed above, when user attached monitor device 900 connects with a non-associated device, the device identification of user attached monitor device 900 is provided to the non-associated device. In turn, the non-associated device that received the identification information from the user attached monitor device reports the identification received from the user attached monitor device and the location of the non-associated device to a third-party location reporting system. The third-party location reporting system in turn transfers the received identification and location information to a recipient registered with the received identification in the third-party location reporting system. In such a case, a location of the non-associated device that provided the identification of the user attached monitor device to the third-party location reporting system is established as the location of the user attached monitor device. The frequency at which communications between the user attached monitor device and a non-associated device may vary depending upon an operational status of the user attached monitor device.

The default time period for attempting to communicate with a user attached monitor device is referred to as the first time. This first time is relatively long compared to a second time which is discussed below. In some embodiments, the first time is used when there is no indication that the user attached monitor device has been removed from the monitored individual and where a connection with a user detached monitor device associated with the monitored individual was recently established. In such a situation, the location of the user attached monitor device is established as the location of the user detached monitor device, and any third-party location information generated by connecting with a non-associated device is only used to determine that the location information from the user detached monitor device is not being illegitimately modified. As such, in some embodiments, the first time is once every seventy-two (72) hours. In some cases, the first time may be continuously modified to occur between once every forty-eight (48) hours and once every ninety-six (96) hours using a random number generated by the controller circuit selecting a random period to avoid predictability.

It is determined whether the user attached monitor device recently established communication with the user detached monitor device via the short-range transceiver (block 1408). In some embodiments a recent connection is a connection within a defined time period. In some cases, a controller circuit of the user attached monitor device is configured to run a continuous timer that is reset whenever a connection is established with the user detached monitor device. In some such embodiments, a recent connection is selected to be any connection within one hour. Based upon the disclosure provided herein, one of ordinary skill in the art will recognize other time periods that may be selected to define a recent connection.

Where a recent connection has been established (block 1408), the connection timer is set to the first time (block 1412). Alternatively, where a connection has not been established with the user detached monitor device within the defined time period (block 1408), the connection timer is set to a second time (block 1410). In contrast to the first time, the second time is selected whenever an undesired operational status (e.g., an indication of a tamper, an indication of a removal, and/or a failure to connect to the user attached monitor device) has occurred. The user attached monitor device may have failed to connect to the user detached monitor device for an extended period of time (block 1408) because, for example, the battery of the user detached monitor device is depleted, the user detached monitor device has been lost, or another situation affecting the user detached monitor device. Where this occurs, it is assumed that the user attached monitor device remains attached to the monitored individual and that the location of the user attached monitor device indicates a location of the monitored individual. As such, the frequency of attempts to connect to non-associated device is increased as this is the best location data available for the monitored individual (i.e., the second time is less than the first time). In some embodiments, the second time is once per hour. Based upon the disclosure provided herein, one of ordinary skill in the art will recognize other values for the second time that may be used in relation to different embodiments.

It is determined whether a proximity sensor indicates removal of the user attached monitor device from the monitored individual (block 1414). Where removal is indicated (block 1414), a removal flag is set (block 1416). This removal flag may be maintained in the memory of the user attached monitor device and is set and unset under control of the controller circuit. It is determined whether a tamper sensor indicates tampering with the user attached monitor device (block 1418). Where tampering is indicated (block 1418), a tamper flag is set (block 1420). This tamper flag may be maintained in the memory of the user attached monitor device and is set and unset under control of the controller circuit. The tamper flag and the removal flag remain set until reset by the controller circuit based upon a received command as discussed above.

Where either the tamper flag or the removal flag is set (block 1422), the connection timer is set to a third time (block 1424). As setting of either the tamper flag or the removal flag indicates that the user attached monitor device has been removed either permanently or temporarily from the monitored individual, establishing location of the monitored individual based upon the user attached monitor device is less likely to be meaningful, and thus the frequency of the connection attempts to non-associated devices is reduced (i.e., the third time is less than the first time). This preserves battery life while occasionally re-establishing location. Where either the user attached monitor device is re-attached to the monitored individual or one or both of the tamper sensor or proximity sensor did not work properly, the updated location status from the user detached monitor device coupled with the low frequency of location data from non-associated devices indicate the need to bring the monitored individual to setup a new user attached monitor device.

It is determined whether the connection timer indicates that it is time to attempt connection to a non-associated device (block 1426). This connection timer uses the selected one of the first time, the second time, or the third time to determine whether it is time to attempt connection. Where it is time to attempt connection (block 1426), the power of the short-range transceiver is increased to allow for communication with devices at a greater distance (block 1428). Again, any connection with a non-associated device results in the device identification of the user attached monitor device being reported to a central monitoring station along with the location of the non-associated device. Once either a connection with a non-associated device has been accomplished or an attempt timeout period expires, the power of the short-range transceiver is reduced to the power that would be used for establishing a connection with the user detached monitor device (block 1430).

In parallel, anytime user detached monitor device attempts to connect with the user attached monitor device via the short-range transceiver (block 1434), user attached monitor device attaches to the user detached monitor device (block 1436). Thus, for example, where the short-range transceiver supports a BlueTooth™ communication protocol, a BlueTooth™ request is received and a corresponding response is sent. The distance at which the communication is completed is governed, at least in part, on the power used by the short-range transceiver which is set to support a maximum distance at which the user attached monitor device is expected to be from the user detached monitor device. Establishing the connection signals that the user attached monitor device is within a defined radius of the user attached monitor device, and therefore the location of the user detached monitor device can be used as a reasonable proxy of the location of the monitored individual. Once the connection has been established (block 1436), the recent connection timer (i.e., the timer indicating the last time a connection was established) is reset and the connection is disconnected (block 1438). This process of connecting and disconnecting is repeated at a user programmable frequency (or under a special circumstance) and under control of the user detached monitor device as more fully described in relation to FIG. 10*b*.

Figure 10B:
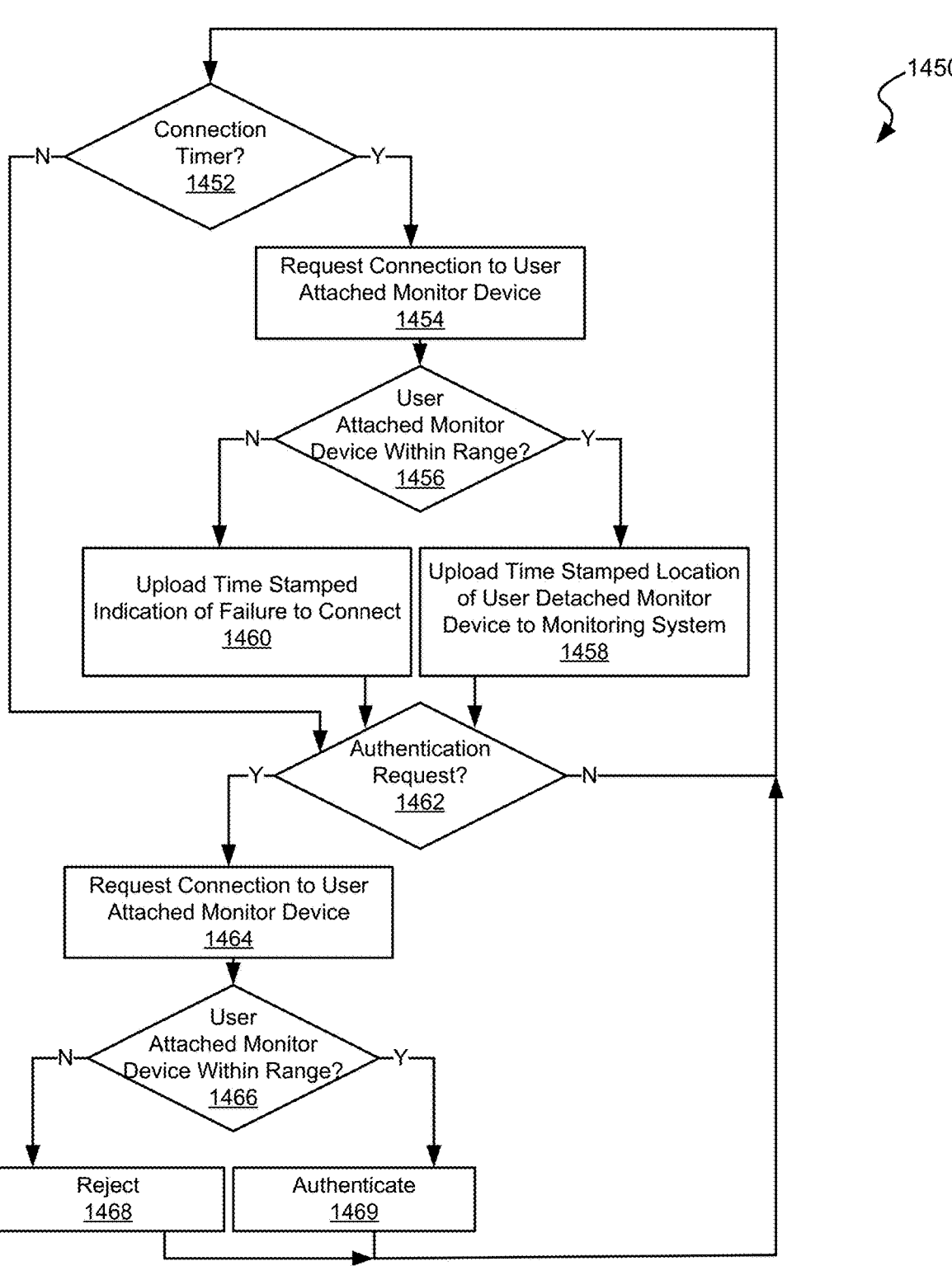

Turning to FIG. 10*b*, a flow diagram 1450 shows a method for operating a user detached monitor device in relation to a user attached monitor device in accordance with some embodiments. Following flow diagram 1450, it is determined if it is time to update the location of a monitored individual to which the user attached monitor device is attached (block 1452). In some embodiments, the time period at which the location is updated is user programmable and a timer monitoring the time period is executed by a timer implemented in a processor of the user detached monitor device.

Figure 11:
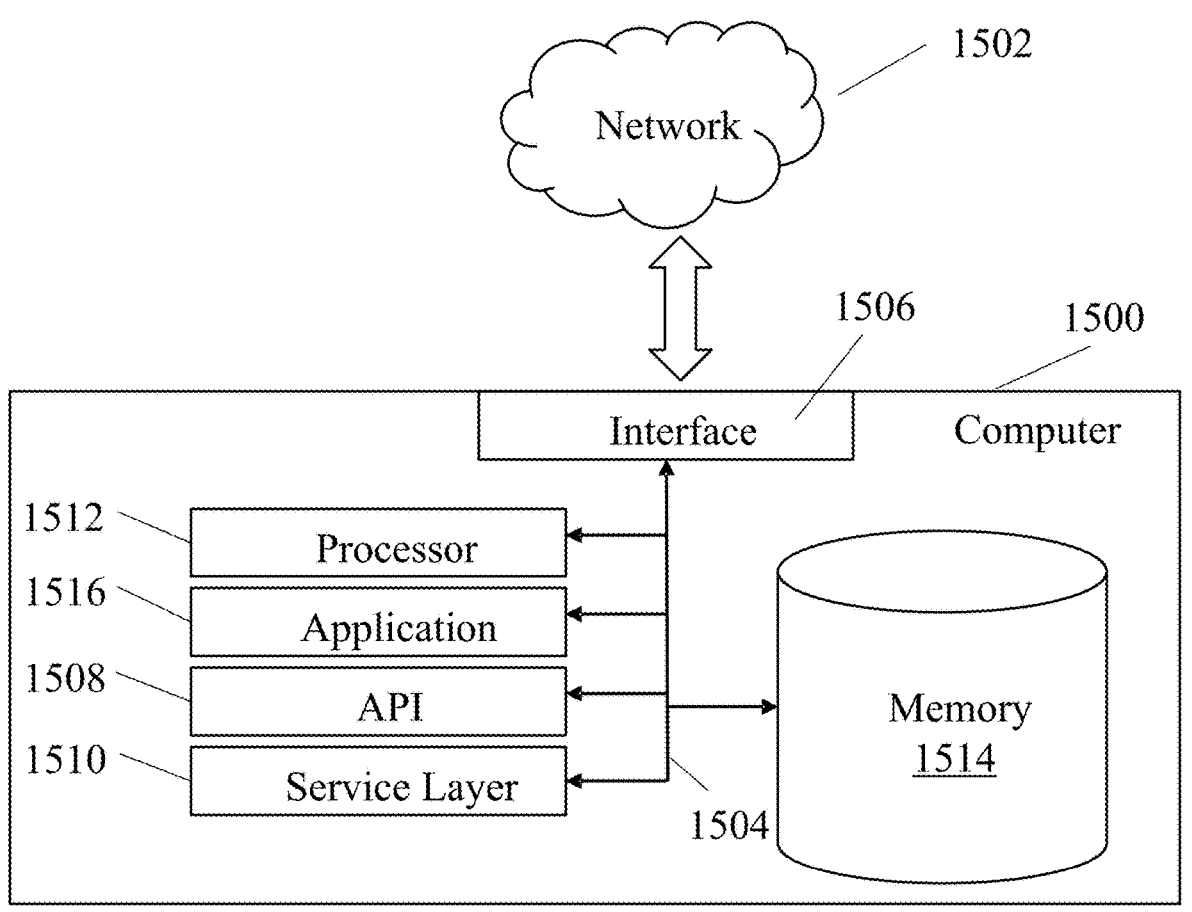
FIG. 11 shows an example processing system that may be used in relation to various embodiments.

In some embodiments, the processes of FIG. 10*b* are implemented as computer executable instructions maintained in a memory on a user detached monitor device and executed by a processor communicably coupled to the aforementioned memory to perform the processes. FIG. 11 shows an example processing system that may be included in the user detached monitor device.

When it is time to update the location information (block 1452), a connection with the user attached monitor device is requested (block 1454). Where, for example, the user attached monitor device communicates via a BlueTooth™ communication protocol, a BlueTooth™ request is sent to connect to the user attached monitor device. It is determined whether the user attached monitor device is within range based upon whether the requested connection was established (block 1456). The distance at which the communication is completed is governed, at least in part, on the power used by the short-range transceiver of the user attached monitor device which is set to support a maximum distance at which the user attached monitor device is expected to be from the user detached monitor device. Establishing the connection signals that the user attached monitor device is within a defined radius of the user attached monitor device, and therefore the location of the user detached monitor device can be used as a reasonable proxy of the location of the monitored individual.

Where the requested connection is not established (block 1456), a time stamped indication of the failed connection is uploaded to a monitoring system (e.g., central monitoring station)(block 1460). Alternatively, where the requested connection is established (block 1456), a current location of the user detached monitor device is time stamped and uploaded to the monitoring system (block 1458). Where the user detached monitor device is a mobile phone, the location information may be accessible from a location services application on the mobile phone. In some cases, the location information may derived from GNSS circuitry on the mobile phone.

It is determined whether an authentication request has been received (block 1462). Such an authentication request may be generated when, for example, someone using the user detached monitor device to access a secure application representing themselves as the individual to which the user attached monitor device is secured. Where an authentication request is received (block 1462), a connection with the user attached monitor device is requested (block 1464). Where, for example, the user attached monitor device communicates via a BlueTooth™ communication protocol, a BlueTooth™ request is sent to connect to the user attached monitor device. It is determined whether the user attached monitor device is within range based upon whether the requested connection was established (block 1466). Again, the distance at which the communication is completed is governed, at least in part, on the power used by the short-range transceiver of the user attached monitor device which is set to support a maximum distance at which the user attached monitor device is expected to be from the user detached monitor device. Establishing the connection signals that the user attached monitor device is within a defined radius of the user attached monitor device, and therefore the location of the user detached monitor device can be used as a reasonable proxy of the location of the monitored individual.

Where the requested connection is not established (block 1466), the authentication request is rejected (block 1468) under an assumption that the person using the user detached monitor device is not the individual to which the user attached monitor device is secured. Alternatively, where the requested connection is established (block 1466), the request is authenticated (block 1469) under an assumption that the person using the user detached monitor device is the individual to which the user attached monitor device is secured. Such an authentication process may offer an additional degree of security to an owner of user detached monitor device by requiring another authentication factor.

Figure 10C:
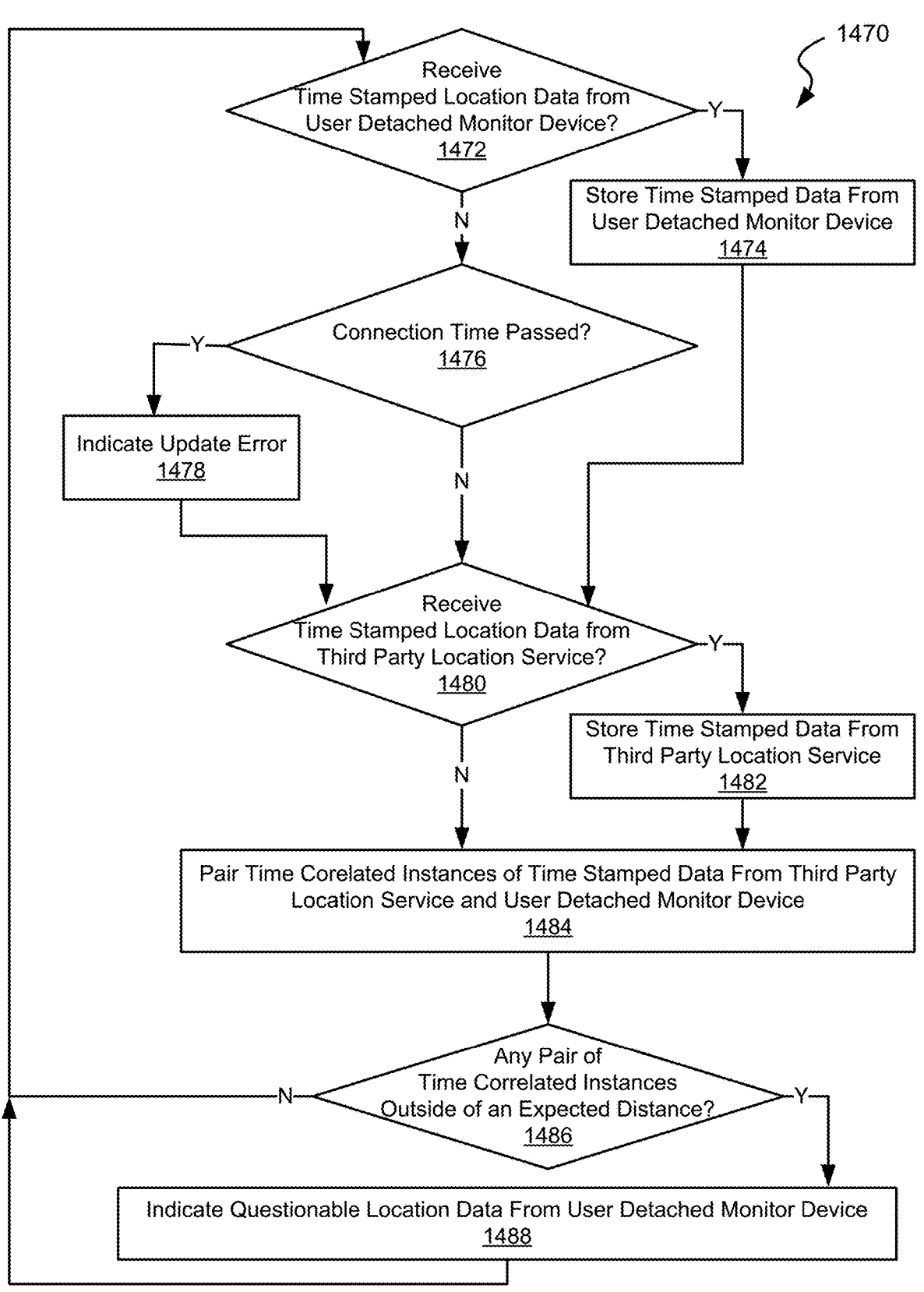

Turning to FIG. 10*c*, a flow diagram 1470 shows a method for operating a central monitoring station in relation to a user attached monitor device, a user detached monitor device, and/or a third-party location reporting system in accordance with some embodiments. In some embodiments, the processes of FIG. 10*c* are implemented as computer executable instructions maintained in a memory on a central monitoring station and executed by a processor communicably coupled to the aforementioned memory to perform the processes. FIG. 11 shows an example processing system that may be included in the central monitoring station.

Following flow diagram 1470, it is determined if a time stamped location data has been received from a user detached monitor device (block 1472). Location information is expected to be updated periodically. Such location information is the location of the user detached monitor device which connects to a user attached monitor device attached to a monitored individual. As the maximum distance at which the user attached monitor device is capable of attaching to the user detached monitor device is relatively short (e.g., less than five (5) meters)), the location of the user detached monitor device is accepted as the location of the monitored individual. In some embodiments, the time period at which the location information is updated by the user detached monitor device and then uploaded to the central monitoring station is user programmable and a timer monitoring the time period is executed by a timer implemented in a processor of the user detached monitor device.

Where location information is received from the user detached monitor device (block 1472), the time stamped data from the user detached monitor device is stored to a memory local to the central monitoring station (block 1474). This information may include, but is not limited to, the device identification of the user attached monitor device attached to the monitored individual, the location of the user detached monitor device, and the time at which the location of the user detached monitor device was obtained. Based upon the disclosure provided herein, one of ordinary skill in the art will recognize a variety of data that may be received and stored.

Alternatively, where location information is not received from the user detached monitor device (block 1472), it is determined if a time period has passed (block 1476). In some embodiments, the time period is user programmable and in particular embodiments the time period is approximately two (2) times the time period where the user detached monitor device is expected to send data. Where the time period expires without receiving time stamped location information (block 1476), an update error is indicated (block 1478). The update error indicates that an expected location information transmission was not received. This can occur, for example, where the user detached monitor device is out of service because, for example, it is out of communication range (e.g., out of range of a wide area wireless network) and/or has a dead battery.

It is determined whether time stamped location data has been received from a third-party location service (block 1480). The third-party location data is provided when the user attached monitor device connects to a non-associated device. In turn, the non-associated device communicates the device identification of the user attached monitor device attached to the monitored individual, the location of the non-associated device, and a time-stamp indicating the time when the location was obtained to a third-party location reporting system, and the third-party location reporting system forwards the information to the central monitoring station. As the maximum distance at which the user attached monitor device is capable of attaching to a non-associated device is relatively short (e.g., less than ten (10) meters)), the location of the non-associated device is accepted as the location of the monitored individual. Location from the third-party location service may be received periodically to be used as a check on whether the location information from the user detached monitor device is reliable, and/or when there is no connection between the user attached monitor device and the user detached monitor device as described above.

Where location information is received from a third-party location service (block 1480), the time stamped data from the third-party location service is stored to a memory local to the central monitoring station (block 1482). As suggested above, this information may include, but is not limited to, the device identification of the user attached monitor device attached to the monitored individual, the location of the non-associated device, and the time at which the location of the non-associated device was obtained. Based upon the disclosure provided herein, one of ordinary skill in the art will recognize a variety of data that may be received and stored.

Time correlated instances of location information from the third-party location service and the user detached monitor device are paired (block 1484). This may include, for example, accessing each time-stamped location data received from the user detached monitor device, and searching the memory for a time-stamped location data from a third-party location service that was received within a defined time of the data from the user detached monitor device. In some embodiments, the defined time is user programmable. In various embodiments, the defined time is ten (10) minutes. Each time a time-stamped location data received from the user detached monitor device and a time-stamped location data from a third-party location service are found within the defined time period, a pair of time correlated instances is created.

For each pair of time correlated instances, it is determined if the location information from the user detached monitor device and the location information from the third party location service are within an expected radius of each other (block 1486). In some embodiments, the expected radius is user programmable. In various embodiments, the expected radius is programmed to be slightly larger than the sum of the maximum communication distance from a user attached monitor device to a user detached monitor device and the maximum communication distance from the user attached monitor device to a non-associated device. Thus, for example, where the maximum communication distance from a user attached monitor device to a user detached monitor device is five (5) meters and the maximum communication distance from a user attached monitor device to a non-associated device is ten (10) meters, the expected distance may be programs as eighteen (18) meters (i.e., the sum of the two maximum distances plus twenty (20) percent). Based upon the disclosure provided herein, one of ordinary skill in the art will recognize a variety of expected distances that may be used in relation to different embodiments.

Where it is determined that the location information from the user detached monitor device and the location information from the third-party location service are not within the expected distance of each other (block 1486), a questionable location data from the user detached monitor device is indicated (block 1488). This indication may be provided via a display or any communication approach known in the art. Where a questionable location is indicated (block 1488), a user tasked with monitoring the monitored individual may make a determination about whether the location reporting capabilities of the user detached monitor device have been compromised in which case an attempt to contact or apprehend the monitored individual may be made.

Elements, such as, but not limited to, user detached monitor device 320, user detached monitor device 920, third-party location monitoring system 170, user interaction system 185, central monitoring station 160, third-party location monitoring system 270, user interaction system 285, central monitoring station 260, third-party location monitoring system 370, user interaction system 385, and/or central monitoring station 360 may be implemented on a computer system. FIG. 11 is a block diagram of a computer system 1500 used to provide computational functionalities associated with described algorithms, methods, functions, processes, flows, and procedures as described in the instant disclosure, according to an implementation. Computer system 1500 is one example of a large number of computer systems that may be used to implement different embodiments. Based upon the disclosure provided herein, one of ordinary skill in the art will recognize a wide variety of computer systems that may be used in relation to different embodiments.

Computer system 1500 is intended to encompass any computing device such as a high-performance computing (HPC) device, a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, computer system 1500 may include a computer that includes an input device, such as a keypad, keyboard, touch screen, or other device that can accept user information, and an output device that conveys information associated with the operation of computer system 1500, including digital data, visual, or audio information (or a combination of information), or a GUI.

Computer system 1500 can serve in a role as a client, network component, a server, a database or other persistency, or any other component (or a combination of roles) of a computer system for performing the subject matter described in the instant disclosure. Computer system 1500 is communicably coupled with a network 1502. In some implementations, one or more components of computer system 1500 may be configured to operate within environments, including cloud-computing-based, local, global, or other environment (or a combination of environments).

At a high level, computer system 1500 is an electronic computing device operable to receive, transmit, process, store, or manage data and information associated with the described subject matter. According to some implementations, computer system 1500 may also include or be communicably coupled with an application server, e-mail server, web server, caching server, streaming data server, business intelligence (BI) server, or other server (or a combination of servers).

Computer system 1500 can receive requests over network 1502 from a client application (for example, executing on another computer system (not shown) and responding to the received requests by processing the said requests in an appropriate software application. In addition, requests may also be sent to computer system 1500 from internal users (for example, from a command console or by other appropriate access method), external or third-parties, other automated applications, as well as any other appropriate entities, individuals, systems, or computers.

Each of the components of computer system 1500 can communicate using a system bus 1504. In some implementations, any or all of the components of the computer system 1500, both hardware or software (or a combination of hardware and software), may interface with each other or interface 1506 (or a combination of both) over system bus 1504 using an application programming interface (API) 1508 or a service layer 1510 (or a combination of API 1508 and service layer 1510. API 1508 may include specifications for routines, data structures, and object classes. API 1508 may be either computer-language independent or dependent and refer to a complete interface, a single function, or even a set of APIs. Service layer 1510 provides software services to computer system 1500 or other components (whether or not illustrated) that are communicably coupled to computer system 1500. The functionality of computer system 1500 may be accessible for all service consumers using this service layer. Software services, such as those provided by service layer 1510, provide reusable, defined business functionalities through a defined interface. For example, the interface may be software written in JAVA, C++, or other suitable language providing data in extensible markup language (XML) format or other suitable format. While illustrated as an integrated component of computer system 1500, alternative implementations may illustrate API 1508 or service layer 1510 as stand-alone components in relation to other components of computer system 1500 or other components (whether or not illustrated) that are communicably coupled to computer system 1500. Moreover, any or all parts of API 1508 or service layer 1510 may be implemented as child or sub-modules of another software module, enterprise application, or hardware module without departing from the scope of this disclosure.

Computer system 1500 includes an interface 1506. Although illustrated as a single interface 1506 in FIG. 11, two or more interfaces 1506 may be used according to particular needs, desires, or particular implementations of computer system 1500. Interface 1506 is used by computer system 1500 for communicating with other systems in a distributed environment that are connected to the network 1502. Generally, the interface 1506 includes logic encoded in software or hardware (or a combination of software and hardware) and operable to communicate with the network 1502. More specifically, the interface 1506 may include software supporting one or more communication protocols associated with communications such that the network 1502 or interface's hardware is operable to communicate physical signals within and outside of the illustrated computer system 1500.

Computer system 1500 includes at least one computer processor 1512. Although illustrated as a single computer processor 1512 in FIG. 11, two or more processors may be used according to particular needs, desires, or particular implementations of computer system 1500. Generally, the computer processor 1512 executes instructions and manipulates data to perform the operations of computer system 1500 and any algorithms, methods, functions, processes, flows, and procedures as described in the instant disclosure.

Computer system 1500 also includes a memory 1514 that holds data for computer system 1500 or other components (or a combination of both) that may be connected to the network 1502. For example, memory 1514 may be a database storing data consistent with this disclosure. Although illustrated as a single memory 1514 in FIG. 11, two or more memories may be used according to particular needs, desires, or particular implementations of computer system 1500 and the described functionality. While memory 1514 is illustrated as an integral component of computer system 1500, in alternative implementations, memory 1514 may be external to computer system 1500.

In addition to holding data, the memory may be a nontransitory medium storing computer readable instruction capable of execution by computer processor 1512 and having the functionality for carrying out manipulation of the data including mathematical computations.

Application 1516 is an algorithmic software engine providing functionality according to particular needs, desires, or particular implementations of computer system 1500, particularly with respect to functionality described in this disclosure. For example, application 1516 can serve as one or more components, modules, applications, etc. Further, although illustrated as a single application 1516, application 1516 may be implemented as multiple applications 1516 on computer system 1500. In addition, although illustrated as integral to computer system 1500, in alternative implementations, application 1516 may be external to computer system 1500.

There may be any number of computers 1500 associated with, or external to, a computer system containing computer system 1500, each computer system 1500 communicating over network 1502. Further, the term "client," "user," and other appropriate terminology may be used interchangeably as appropriate without departing from the scope of this disclosure. Moreover, this disclosure contemplates that many users may use one computer system 1500, or that one user may use multiple computers 1500.

In some embodiments, computer system 1500 is implemented as part of a cloud computing system. For example, a cloud computing system may include one or more remote servers along with various other cloud components, such as cloud storage units and edge servers. In particular, a cloud computing system may perform one or more computing operations without direct active management by a user device or local computer system. As such, a cloud computing system may have different functions distributed over multiple locations from a central server, which may be performed using one or more Internet connections. More specifically, cloud computing system may operate according to one or more service models, such as infrastructure as a service (IaaS), platform as a service (PaaS), software as a service (SaaS), mobile "backend" as a service (MBaaS), serverless computing, artificial intelligence (AI) as a service (AIaaS), and/or function as a service (FaaS).

In conclusion, the present invention provides for novel systems, devices, and methods for providing location information for a tracking device. While detailed descriptions of one or more embodiments of the invention have been given above, various alternatives, modifications, and equivalents will be apparent to those skilled in the art without varying from the spirit of the invention. Therefore, the above description should not be taken as limiting the scope of the invention, which is defined by the appended claims.

What is claimed is:

1. A method for identifying questionable tracking data, the method comprising:

receiving a first location data from a user detached monitor device, wherein the first location data includes a first location of the user detached monitor device obtained at a first time, and wherein the user detached monitor device is configured to connect to a user attached monitor device;

receiving a second location data from a third-party location service, wherein the second location data includes a second location of a non-associated device to which the user attached monitor device connected, wherein the second location was obtained at a second time;

determining, by a processing resource, that a difference between the first time and the second time is within a defined period of time;

determining, by the processing resource, that a distance between the first location and the second location is greater than an expected distance; and indicating, by the processing resource, a questionable location from the user detached monitor device based on the distance between the first location and the second location being greater than the expected distance.

2. The method of claim 1, wherein the user attached monitor device is configured to connect to the user detached monitor device within a first maximum distance; wherein the user attached monitor device is configured to connect to non-associated device within a second maximum distance.

3. The method of claim 2, wherein the first maximum distance is the same as the second maximum distance.

4. The method of claim 2, wherein the first maximum distance is less than five meters and the second maximum distance is less than ten meters.

5. The method of claim 2, wherein the expected distance is greater than or equal to a sum of the first maximum distance and the second maximum distance.

6. The method of claim 1, wherein the expected distance is user programmable.

7. The method of claim 1, wherein the period of time is user programmable.

8. The method of claim 1, wherein the first location data includes a time stamp indicating when the first location was obtained and a device identification of the user attached monitor device.

9. The method of claim 1, wherein the second location data includes a time stamp indicating when the second location was obtained and a device identification of the user attached monitor device.

10. The method of claim 1, wherein the processing resource is communicably coupled to a display, and wherein indicating the questionable location from the user detached monitor device includes displaying a message indicating the questionable location on the display.

11. The method of claim 1, wherein the user detached monitor device is a mobile phone.

12. A monitoring system, the system comprising:

a user attached monitor device including:

a strap configured for attachment to a monitored individual;

a wireless transceiver configured to connect to a first wireless device within a first defined range and a second wireless device within a second defined range; and a status indicator configured to detect a status of the user attached monitor device;

the first wireless device assigned to the monitored individual and including:

a first location subsystem configured to obtain a first location of the first wireless device;

a clock configured to time stamp the first location with a first time corresponding to obtaining the first location;

a central monitoring station configured to:

receive the first time and the first location directly from the first wireless device;

receive a second location of the second wireless device and a time stamp for the second location from a third party location service with which the second wireless device is associated;

determine that a difference between the first time and the second time is within a defined period of time;

determine that a distance between the first location and the second location is greater than an expected distance; and indicate a questionable location from the first wireless device based on the distance between the first location and the second location being greater than the expected distance.

13. The system of claim 12, wherein the first defined range is the same as the second defined range.

14. The system of claim 12, wherein the first defined range is less than five meters and the second defined range is less than ten meters.

15. The system of claim 12, wherein the expected distance is greater than or equal to a sum of the first defined range and the second defined range.

16. The system of claim 12, wherein the expected distance is user programmable.

17. The system of claim 12, wherein the period of time is user programmable.

18. The system of claim 12, wherein the first defined range is less than the second defined range, and wherein a power of the wireless transceiver is increased to connect out to the second defined range based at least in part on the status of the user attached monitor device.

19. The system of claim 18, wherein the status of the user attached monitor device is selected from a group consisting of: occurrence of a timeout condition; detection of tampering with the user attached monitor device, and a change in proximity between the user attached monitor device and the monitored individual.

20. A user attached monitor device, the user attached monitor device comprising:

a strap configured for attachment to a monitored individual;

a wireless transceiver configured to connect to a first wireless device within a first defined range and a second wireless device within a second defined range, wherein the first defined range is less than the second defined range; and a status indicator configured to detect a status of the user attached monitor device, wherein the status of the user attached monitor device is selected from a group consisting of: occurrence of a timeout condition; detection of tampering with the user attached monitor device, and a change in proximity between the user attached monitor device and the monitored individual; and wherein a power of the wireless transceiver is increased to connect out to the second defined range based at least in part on the status of the user attached monitor device.

* * * * *